United States Patent
Wadhwa et al.

(10) Patent No.: US 10,131,922 B2
(45) Date of Patent: Nov. 20, 2018

(54) INCREASE PRODUCTION OF ISOPRENOIDS IN SACCHAROMYCES CEREVISIAE BY CAROTENOID OPTIMIZATION AND SCREENING

(71) Applicant: Indian Institute of Science Education and Research, Punjab (IN)

(72) Inventors: Manisha Wadhwa, Punjab (IN); Anand Kumar Bachhawat, Punjab (IN)

(73) Assignee: Indian Institute of Science Education and Research, Punjab (IN)

( * ) Notice: Subject to any disclaimer, the term of this patent is extended or adjusted under 35 U.S.C. 154(b) by 0 days.

(21) Appl. No.: 15/066,296

(22) Filed: Mar. 10, 2016

(65) Prior Publication Data
US 2017/0198310 A1   Jul. 13, 2017

(30) Foreign Application Priority Data

Mar. 10, 2015 (IN) .............................. 642/DEL/2015

(51) Int. Cl.
| | |
|---|---|
| C12P 23/00 | (2006.01) |
| C12N 9/04 | (2006.01) |
| C12P 5/00 | (2006.01) |
| C12N 15/52 | (2006.01) |
| C12N 15/81 | (2006.01) |
| C12N 9/88 | (2006.01) |

(52) U.S. Cl.
CPC ............... *C12P 5/007* (2013.01); *C12N 9/88* (2013.01); *C12N 15/52* (2013.01); *C12N 15/81* (2013.01); *C12Y 402/03* (2013.01)

(58) Field of Classification Search
CPC combination set(s) only.
See application file for complete search history.

(56) References Cited

U.S. PATENT DOCUMENTS

2011/0041218 A1   2/2011   Schalk

OTHER PUBLICATIONS

Parayil Kumaran Ajikumar, et al.; Isoprenoid Pathway Optimization for Taxol Precursor Overproduction in *Escherichia coli*; Science Mag.; Oct. 1, 2010; pp. 70-74; vol. 330.
Hal Alper, et al. Engineering Yeast Transcription Machinery for Improved Ethanol Tolerance and Production; Science Mag.; Dec. 8, 2006; pp. 1565-1568; vol. 314.
Hal Alper, et al.; Global Transcription Machinery Engineering: A new Approach for Improving Cellular Pheotype; Science Direct; Jan. 8, 2007; pp. 258-267.
Salim Al-Babili, et al.; Exploring the Potential of the Bacterial Carotene Desaturase Crtl to Increase the B-Carotene Content in Golden Rice; Journal of Experimental Botany; Feb. 17, 2006; pp. 1007-1014; vol. 57, No. 4.
Michael Bleichenbacher, et al.; Novel Interactions Between the Components of Human and Yeast TFIIA/TBP/DNA Complexes; Science Direct; 2003; pp. 783-793.
Jorg Bohlmann, et al.; Terpenoid Biomaterials; The Plant Journal; 2008; pp. 656-669; vol. 54.
Anne Caniard, et al.; Discovery and Functional Characterization of two Diterpene Synthases for Sclareol Biosynthesis in *Salvia sclarea* (L) and their Relevance for Perfume Manufacture; BCM Plant Biology; 2012; pp. 1-13.
Daniel I. Chasman, et al.; Crystal Structure of Yeast TATA-Binding Protein and Model for Interaction with DNA; Proc. Natl. Acad. Sci. USA; Sep. 1993; pp. 8174-8178; vol. 90.
Wenjing Guo, et al.; Lycopene Cyclase and Phytoene Synthase Activities in the Marine Yeast Rhodosporidium Diobovatum are Encoded by a Single Gene crtYB; Journal of Basic Microbiology; 2014; pp. 1053-1061.
William N. Hunter; The Non-Mevolonate Pathway of Isoprenoid Precursor Biosynthesis; Journal of Biological Chemistry; Jul. 27, 2007; pp. 21573-21577; vol. 282.
Yu Jiang, et al.; BTS1 Encodes a Geranylgeranyl Diphosphate Synthase in *Saccharomyces cerevisiae*; The Journal of Biological Chemistry; Sep. 15, 1995; pp. 21793-21799; vol. 270, No. 37.
Shailesh Kumar, et al.; Genome Sequence of the Oleaginous Red Yeast Rhodosporidium Toruloides MTCC 457; Journals ASM; Aug. 2012; pp. 1083-1084; vol. 11, No. 8.
Qian Li, et al.; Enhancing Beta-Carotene Production in *Saccharomyces cerevisiae* by Metabolic Engineering; FEMS Microbiology Letters; 2013; pp. 94-101.
Norihiko Misawa, et al.; Elucidation of the Erwinia Uredovora Carotenoid Biosynthetic Pathway by Functional Analysis of Gene Products Expressed in *Escherichia coli*; Journal of Bacteriology; Dec. 1990; pp. 6704-6712; vol. 172, No. 12.
Martin Moline, et al.; Production of Torularhodin, Torulene, and B-Carotene by Rhodotorula Yeasts; Springer Science+Business Media; 2012; pp. 275-283.
Valerie Nacken, et al.; Probing the Limits of Expression Levels by Varying Promoter Strength and Plasmid Copy Number in *Saccharomyces cerevisiae*; An International Journal on Genes and Genomes; 1996; pp. 253-260; vol. 175.
H.J. Nells, et al.; Microbial Sources of Carotenoid Pigments Used in Foods and Feeds; Journal of Applied Bactenology; 1991; pp. 181-191; vol. 70.
Bilge Ozaydin, et al.; Carotenoid-Based Phenotypic Screen of the Yeast Deletion Collection Reveals New Genes with Roles in Isoprenoid Production; Metabolic Enginerring; 2013; pp. 174-183; vol. 15.
Dae-Kyun Ro, et al; Production of the Antimalarial Drug Precursor Artemisinic Acid in Engineered Yeast; Nature Publishing Group; Apr. 2006; pp. 940-943; vol. 440.
Mark David Rose, et al.; KAR1, A Gene Required for Function of Both Intranuclear and Extranuclear Microtubules in Yeast; Cell; 1987; pp. 1047-1060; vol. 48.

(Continued)

*Primary Examiner* — Kagnew H Gebreyesus
(74) *Attorney, Agent, or Firm* — Colin P. Cahoon; Shaukat A. Karjeker; Carstens & Cahoon, LLP

(57) ABSTRACT

The invention is for an increased isoprenoid production by carotenoid optimization in an expression system and the carotegenic gene for optimization may be geranylgeranyl diphosphate synthase (GGPPS), phytoene synthase (PSY1), conserved CRTI or mutated $CRT1_{A393T}$, BT1 of *S. cerevisae*. The carotogenic gene from red yeast which includes *Rhodosporidium* spp. *Rhodotorula* spp, *Sporidiobolus* spp., *Leucosporidium* spp., *Sporobolomyes* spp. is selected.

Figure 1:
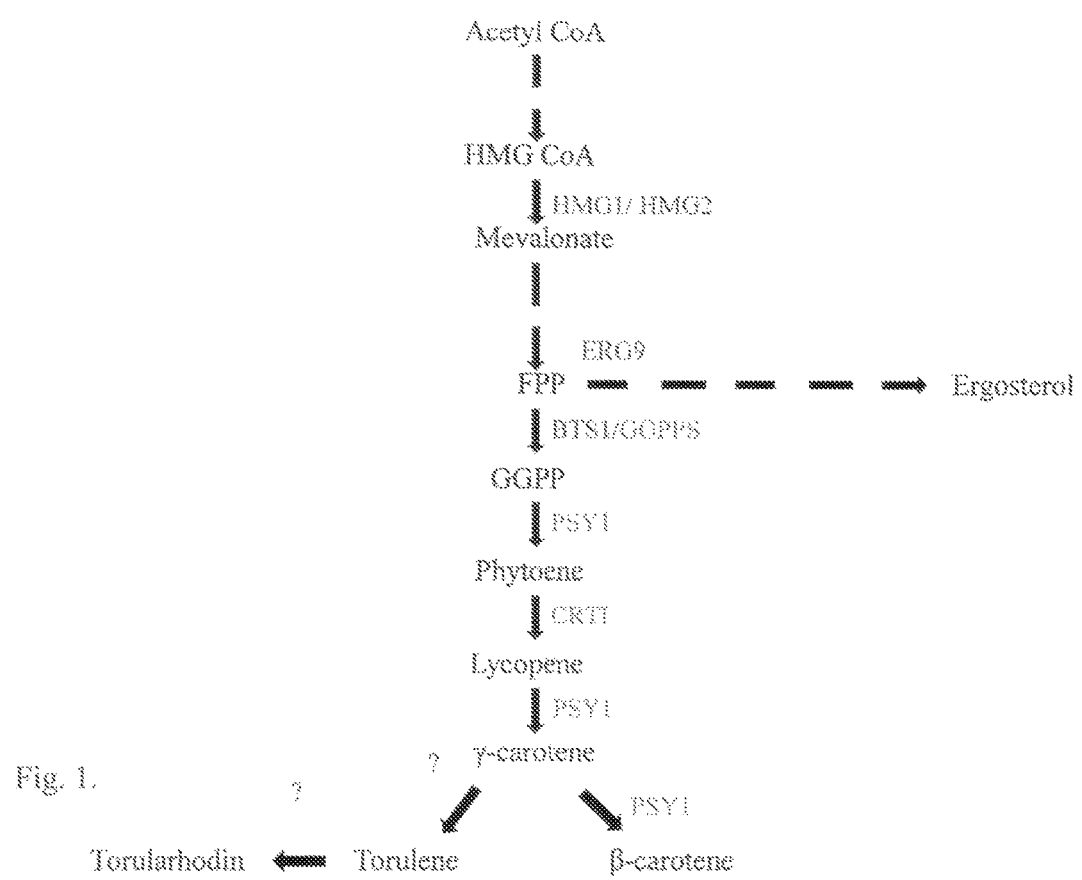

11 Claims, 24 Drawing Sheets
Specification includes a Sequence Listing.

(56) References Cited

OTHER PUBLICATIONS

Balazs Szappanos, et al.; An Integrated Approach to Characterize Genetic Interaction Networks in Yeast Metabolism; Nature America, Inc.; Jul. 2011; pp. 656-664; vol. 43, No. 7.

High-Efficiency Yeast Transformation; Chapter 22; pp. 1799-1801.

Patrick Schaub, et al.; On the Structure and Function of the Phytoene Desaturase CRTI from Pantoea Ananatis, a Membrane-Peripheral and FAD-Dependent Oxidase/Isomerase; PLoS ONE; Jun. 2012; pp. 1-15; vol. 7, Issue 6.

Ken Ukibe, et al.; Metabolic Engineering of *Saccharomyces cerevisiae* for Astaxanthin Production and Oxidative Stress Tolerance; Applied and Environmental Microbiology; Nov. 2009; pp. 7205-7211; vol. 75, No. 22.

Rene Verwaal, et al.; High-Level Production of Beta-Carotene in *Saccharomyces cerevisiae* by Successive Transformation with Carotenogenic Genes from Xanthophyllomyces Dendrorhous; Applied and Environmental Microbiology; Jul. 2007; pp. 4342-4350; vol. 73, No. 13.

Tamara Wriessnegger. et al.; Yeast Metabolic Engineering—Targeting Sterol Metabolism and Terpenoid Formation; Science Direct; Apr. 11, 2013; 17 Pages.

Shigeyuki Yamano, et al.; Metabolic Engineering for Production of B-Carotene and Lycopene in *Saccharomyces cerevisiae*; Biosci. Biotech. Biochem.; 1994; pp. 1112-1114.

Jifeng Yuan, et al.; Combinatorial Engineering of Mevalonate Pathway for Improved Amorpha-4,11-Diene Production in Budding Yeast; Biotechnology and Bioengineering; Mar. 2014; pp. 608-617; vol. 111, No. 3.

Hongwei Zhao, et al.; Improvement of Oxidative Stress Tolerance in *Saccharomyces cerevisiae* Through Global Transcription Machinery Engineering; J Ind Microbial Biotechnol; 2014; pp. 869-878.

Zhiewi Zhu, et al.; A Multi-Omic Map of the Lipid-Producing Yeast Rhodosporidium Toruloides; Nature Communications; Oct. 9, 2012; pp. 1-11.

| | Control | SPT15(R98H) | SPT15(A100V) | SPT15(A101T) |
|---|---|---|---|---|
| β-carotene | 39.05 | 285.39 | 133.86 | 135.27 |
| Phytoene | 0.00 | 88.38 | 36.52 | 10.70 |
| Lycopene | 0.00 | 4.38 | 2.08 | 2.55 |

INCREASE PRODUCTION OF ISOPRENOIDS IN SACCHAROMYCES CEREVISIAE BY CAROTENOID OPTIMIZATION AND SCREENING

FIELD OF INVENTION

The invention is in the field of biotechnology with specific reference to metabolic engineering for increased production of isoprenoid compounds/isoprenoid pigments.

BACKGROUND AND PRIOR ART

Isoprenoids or terpenoids represent the largest class of natural products with more than 40,000 known structures. Many of these terpenoids have immense commercial value. Their biosynthesis in heterologous hosts is relatively easy and cost effective as compared to the chemical synthesis or the extraction from their natural sources. *Saccharomyces cerevisiae* is choice of organism as heterologous host due to its preference by industry. To increase the yield of isoprenoids in yeast, previous efforts were on manipulating the mevalonate pathway. Using known information about the mevalonate-isoprenoid pathway, three potential targets were identified as being potential blocks for isoprenoid biosynthesis, HMG-CoA reductase (3-hydroxy-3-methylglutaryl-Coenzyme A reductase-HMG1), the transcription factor, UPC2, and the ergosterol branch point, squalene synthase ERG9. Using truncated tHMG1 (that lacks feedback regulation), a hyperactive transcription factor sterol regulatory element binding protein (upc2-1) (that increases expression of the mevalonate pathway), or reduced expression of ERG9 (that prevents isoprenoids from branching off), increased flux has been demonstrated and the yield of isoprenoids further increases when these different mutations are combined. However, in the cell, metabolic pathways are interconnected and tightly regulated and it is possible that besides the mevalonate pathway genes, there may be other genes which affect directly or indirectly the yield of carotenoids or other terpenoids produced in yeasts. However, a good genetic screening method is required to identify the same. As carotenoids are colored compounds, their production by yeast cells provides a good visual phenotypic screen. Depending on the level of expression of carotenogenic genes the color imparted varies from faint yellow, yellow to orange. Their color can be used as visual genetic screen for determining flux in the isoprenoid pathway.

Several groups have attempted to increase the flux in the isoprenoid pathway using this carotenoid based visual pigmentation screen using the enzymes from *Xanthophyllomyces dendrorhous*, however these studies have met with limited success, since in all it was observed that increasing the flux in this pathway through known flux increasers such as tHMG1, a decrease in pigmentation was observed. Estimation of carotenoids revealed that the decrease was most likely due to a block at the phytoene dehydrogenase (RtCRTI) step since phytoene was accumulating under these conditions and the increased phytoene (which is colorless) masked any increase in color due to higher β-carotene and prevented the use of visual pigmentation as a genetic screen.

In one study the transformed yeast deletion collection with the carotenogenic plasmids from *Xanthophyllomyces dendrorhous* were screened for altered pigmentation, and it was observed that approximately 1100 deletion strains showed a decrease in color while 156 deletion strains showed an increase in color. Among the latter 5 showed a consistent four-fold increase in carotenoids levels as compared to parent strain. However, when attempts were made to validate the increased flux by examining production of bisabolene in these strains, all strains surprisingly produced less bisabolene than wild type parental strain. The slight increase in bisabolene production in these deletion strains that was eventually achieved was only possible after carrying out several other modifications (such as gene fusions) of the isoprenoid pathway. Thus, the visual screen, which was not validated by known flux increasers (such as tHMG1) did not really succeed in picking up the desired phenotypes.

The red yeasts belonging to the *Rhodotorula* spp., *Rhodosporidium* spp. and *Sporobolomyces* spp. have an intense red color and are considered to have highest β-carotene levels. In addition to β-carotene, these yeasts produce the carotenoids torulene and torularhodin. To overcome the limitations encountered in the increased production of isoprenoid by carotenoid based visual pigmentation screen, the present invention aims to use the carotenogenic genes from these red yeasts and attempts to develop a genetic screen for isoprenoid/carotenoid production in *Saccharomyces cerevisiae*. The carotenoid gene of *Arabidopsis* spp. and plants is also expressed in yeast. The carotenoids of red yeasts are being expressed in *S. cerevisiae* for the first time. The invention seeks first to identify and express these enzymes from this yeast followed by a strategy to develop it as a genetic screen for carotenoid/isoprenoid production by overcoming limiting step i.e desaturation of phytoene by phytoene dehydrogenase. The invention aims to optimize genetic screen by utilizing catalytically efficient mutant of phytoene dehydrogenase. The present invention also aims to increase α-farnesene of the isoprenoid pathway. The present invention also provides two mutant genes—phytoene dehydrogenase (RtCRTI) and SPT15 which increase flux in isoprenoid pathway and hence the yield of carotenoids.

OBJECT OF THE INVENTION

The object of the invention is to develop a recombinant system/construct for increased expression of isoprenoid by optimizing the carotenoid genes.

To develop a screen using a combinations of weak and strong promoters of *S. cerevisiae* to allow for the detection of increased flux through the pathway with tHMG1 expression.

The object of the invention is for a method of optimization of the carotenoid genes and over expression of isoprenoid.

The object of invention is to provide phenotypic V1 genetic screen.

The invention aims at identification and expression of the genes for the core biosynthetic carotenogenic enzymes up to β-carotene from *R. toruloides, Arabidopsis* spp. or plants having 50% homology with carotenoid genes of *Arabidopsis* into *S. cerevisiae*.

To target SPT15 gene for mutagenesis and to isolate mutants showing increase flux in the isoprenoid pathway.

To target phytoene dehydrogenase RtCRTI for mutagenesis and to isolate mutants which are catalytically more efficient.

BRIEF DESCRIPTION OF THE DRAWINGS AND FIGURES

FIG. 1: Depicts the proposed carotenogenic pathway in *Rhodosporidium toruloides*. Carotenogenic pathway of *Rhodosporidium toruloides* for the production of βcarotene consists of three enzymes—Geranylgeranyl diphosphate synthase encoded by RtGGPPS, bifunctional phytoene synthase and lycopene cyclase encoded by RtPSY1 and phytoene dehydrogenase encoded by RtCRTI.

Figures 2A, 2B:
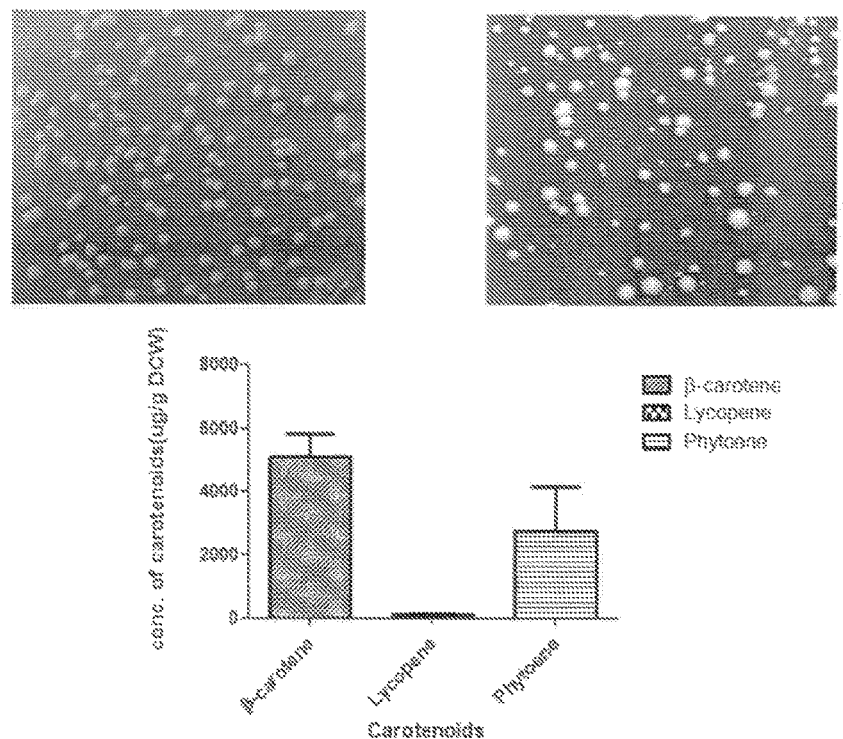

FIG. 2A depicts photos of SD-ura-leu-trp plates for the functional expression of R. toruloides carotenogenic enzymes in S. cerevisiae and FIG. 2B depicts the relative carotenoid levels of R. toruloides expressed in S. cerevisiae.

S. cerevisiae transformants produce orange color when transformed with pRS315-TEF-RtGGPPS, p416TEF-RtPSY1 and pRS314TEF-RtCRTI (2a) and white color when transformed with Empty vectors—pRS315TEF, p416TEF and pRS314TEF (2b). Transformants were grown on SD-ura-leu-trp plates supplemented with appropriate amino acids at 30° C. for 3 days. After 3 days, photographs were taken. (B) Chemical extraction and analysis of carotenoids as given in methods of $TEF_{GGPPS}+TEF_{PSY1}+TEF_{CRTI}$ engineered strain after growth in 500 mL flasks containing 100 mL media for 5 days. Error bars represent the standard error mean of three flasks.

Figure 3:
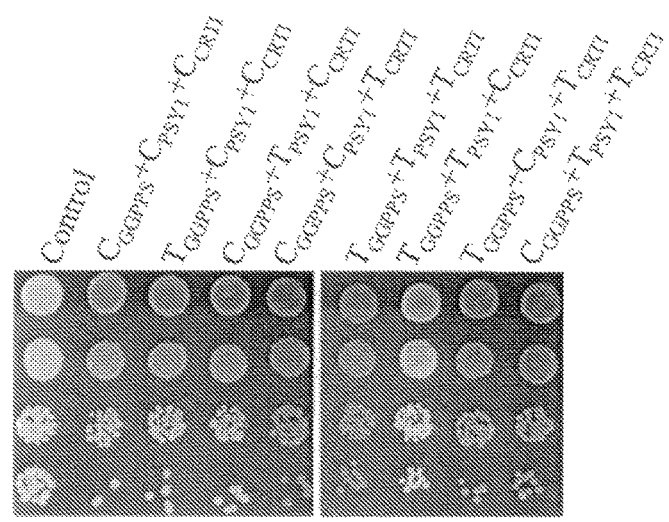

FIG. 3: shows comparison of different promoter combination strains. S. cerevisiae was transformed with different combinations of vector constructs pRS315TEF-RtGGPPS, p416TEF-RtPSY1, pRS314TEF-RtCRTI, pRS315CYC-RtGGPPS, p416CYC-RtPSY1 and pRS314CYC-RtCRTI. Each transformant contain three vector constructs-RtGGPPS, RtPSY1 and RtCRTI genes either from TEF promoter or CYC promoter. Transformants were grown on SD-ura-leu-trp plates supplemented with appropriate amino acids at 30° C. for overnight, and then grown in fresh media till mid log phase. Yeast cells then harvested and dilution spotted on SD-ura-leu-trp plates supplemented with appropriate amino acids at 0.2, 0.02, 0.002, 0.0002 O.D. Plates were incubated at 30° C. for 3 days and then photographs were taken. S. cerevisiae transformants with empty vectors were used as control.

Figures 4A, 4B:
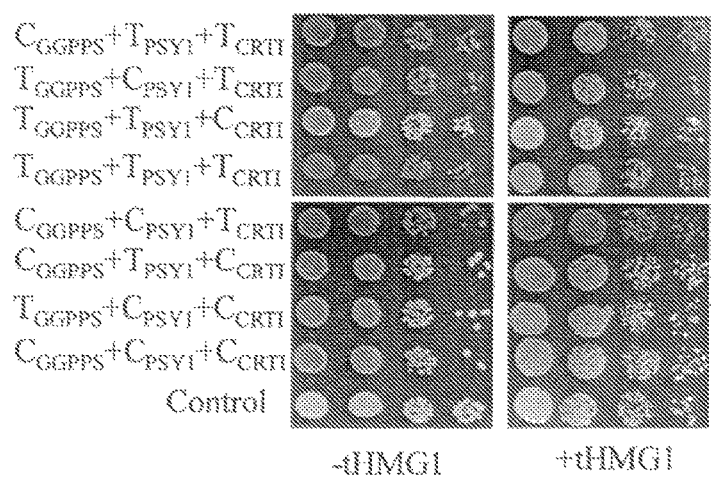

FIG. 4: depicts comparison of different promoter combination strains with and without over expression of tHMG1.

Different promoter combination constructed strains in FIG. 3 were transformed with pRS313TEF-tHMG1 vector construct. Transformants were grown in minimal media supplemented with appropriate amino acids at 30° C. for 3 days and then re inoculated in fresh media till mid log phase. Yeast cells then harvested and dilution spotted on SD-ura-leu-trp plates (depicted in 4A) and SD-ura-leu-trp-his plates (depicted in 4B) supplemented with appropriate amino acids at 0.2, 0.02, 0.002, 0.0002 O.D respectively. Plates were incubated at 30° C. for 3 days and then photographs were taken. S. cerevisiae transformants with empty vectors pRS313TEF were used as control.

Figure 5:
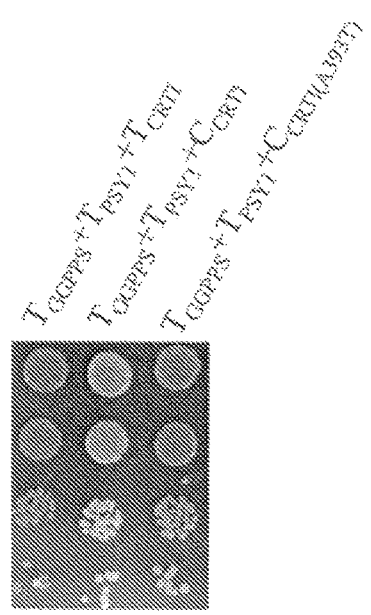

FIG. 5: Depicts catalytically active mutant of phytoene dehydrogenase ($RtCRTI_{A393T}$) to increase pigmentation levels. S. cerevisiae was transformed with pRS315TEF-RtGGPPS+p416TEF-RtPSY1, and +pRS314TEF-RtCRTI, pRS315TEF-RtGGPPS+p416TEF-RtPSY1+pRS314CYC-RtCRTI and pRS315TEF-RtGGPPS+p416TEF-RtPSY1+pRS314CYC-RtCRTI(A393T)). Transformants were grown on minimal media supplemented with appropriate amino acids at 30° C. for 3 days are harvested and dilution spotted on SD-ura-trp-leu plates supplemented with appropriate amino acids at 0.2, 0.02, 0.002, 0.0002 O.D respectively. Plates were incubated at 30° C. for 3 days and then photographs were taken. S. cerevisiae transformants with empty vectors were used as control.

Figure 6:
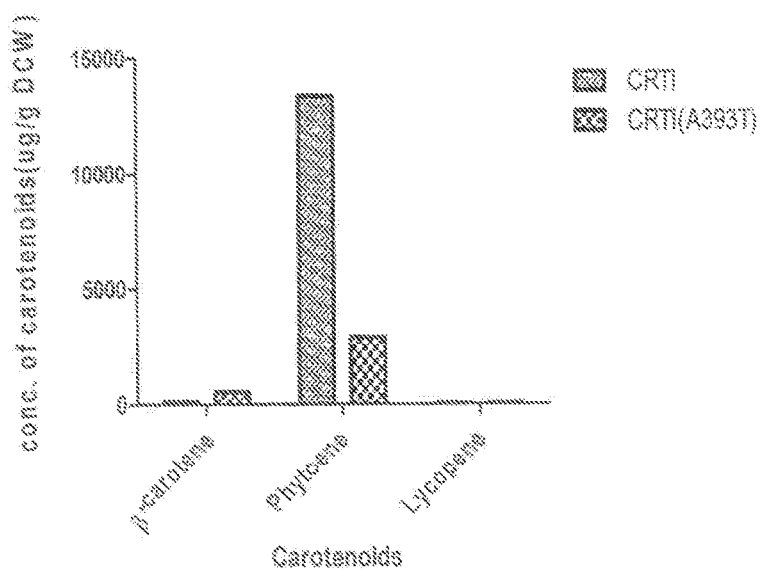

FIG. 6: Representation of the chemical analysis of carotenoids produced by S. cerevisiae strains transformed with pRS315TEF-RtGGPPS+p416TEF-RtPSY1+pRS314CYC-RtCRTI and pRS315TEF-RtGGPPS+p416TEF-RtPSY1+pRS314CYC-RtCRTI(A393T). Cultures were grown in 500 mL flasks containing 100 mL media for 5 days before extraction.

Figure 7:
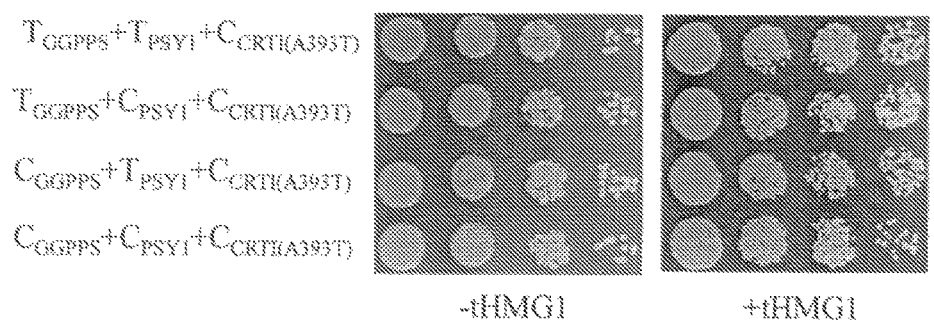

FIG. 7: Photomicrograph of carotenoid producing mutant S. cerevisiae promoter combination strains. S. cerevisiae was transformed with different combination of vector constructs pRS315TEF-RtGGPPS, p416TEF-RtPSY1, pRS314CYC-RtCRTI(A393T), pRS315CYC-RtGGPPS and p416CYC-RtPSY1. Each transformant contains three vector constructs RtGGPPS, RtPSY1 either from TEF or CYC and CYC-RtCRTI(A393T). Transformants were grown in SD minimal media supplemented with appropriate amino acids at 30° C. for overnight. And then reinoculated in fresh media till mid log phase. Yeast cells then harvested and transformed with pRS313TEF-tHMG1 Transformants were grown on SD-ura-leu-trp-his plates supplemented with appropriate amino acids at acids at 30° C. for 3 days. These transformants with over expression of tHMG1 and previous transformants without over expression of tHMG1 were dilution spotted at 0.2, 0.02, 0.002, 0.0002 O.D on SD-ura-leu-trp-his and SD-ura-leu-trp plates supplemented with appropriate amino acids respectively. Plates were incubated at 30° C. for 3 days and then photographs were taken.

Figure 8:
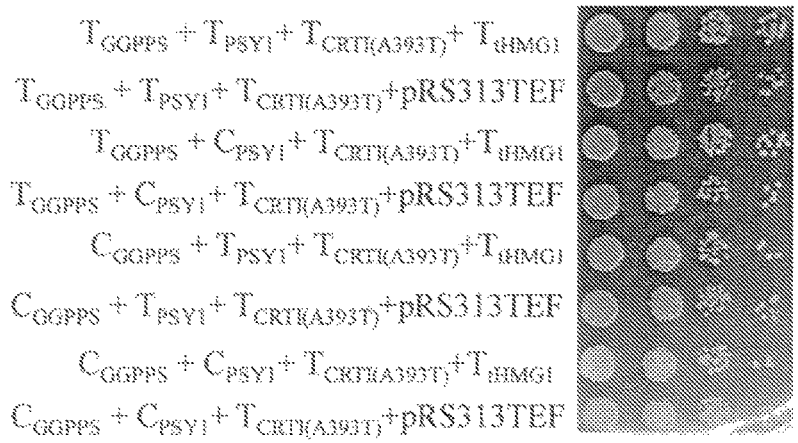

FIG. 8: Photomicrographs of transformants containing mutant RtCRTI (A393T) under TEF promoter. S. cerevisiae was transformed with different combination of vector constructs pRS315TEF-RtGGPPS, p416TEF-RtPSY1, pRS314TEF-RtCRTI(A393T), pRS315CYC-RtGGPPS and p416CYC-RtPSY1, pRS313TEF, pRS313TEF-tHMG1. Each transformant contains four vector constructs RtGGPPS, RtPSY1 either from TEF or CYC and TEF-RtCRTI (A393T) and either pRS313TEF or pRS313TEF-tHMG1. Transformants were grown in minimal media supplemented with appropriate amino acids at 30° C. for overnight. And then inoculated in fresh media till mid log phase. Yeast cells then harvested and dilution spotted on SD-ura-leu-trp-his plates supplemented with appropriate amino acids at 0.2, 0.02, 0.002, 0.0002 O.D. Plates were incubated at 30° C. for 3 days and then photographs were taken.

Figure 9:
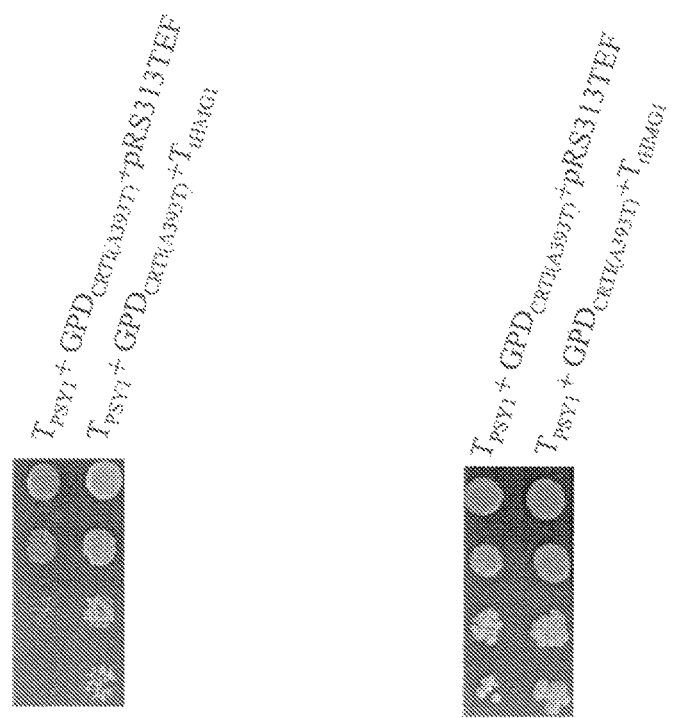

FIG. 9: Photomicrographs of carotenoid producing mutant S. cerevisiae strain. S. cerevisiae was transformed with p416TEF-RtPSY1, pRS315GPD-RtCRTI(A393T) and either with pRS313TEF or pRS313TEF-tHMG1. BTS1 (genomic copy) is under native promoter. Transformants were grown in minimal media supplemented with appropriate amino acids for overnight. And then reinoculated in fresh media till mid log phase. Yeast cells then harvested and dilution spotted on SD-ura-trp-his plates supplemented with appropriate amino acids at 0.2, 0.02, 0.002, 0.0002 O.D. Plates were incubated at 30° C. and photographs were taken after 3 days and 5 days.

Figure 10:
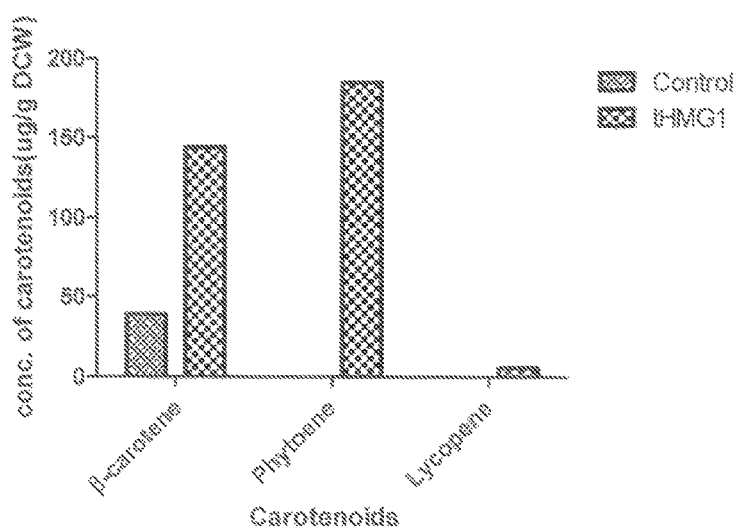

FIG. 10: Representation of chemical analysis of carotenoids produced by "V1 assay strain" with and without tHMG1. S. cerevisiae transformed with p416TEF-RtPSY1+pRS314GPD-RtCRTI(A393T)+pRS313TEF and p416TEF-RtPSY1+pRS314CYC-RtCRTI(A393T)+pRS313TEF-tHMG1. Cultures were grown in 500 mL flasks containing 100 mL media for 5 days before extraction.

Figure 11:
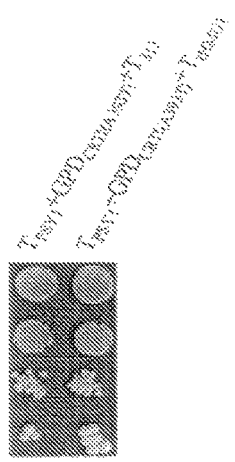

FIG. 11: Photomicrograph showing the effect of tHMG1 on pigmentation of CEN.PK-1C carrying V1 assay strain combination plasmids.

CEN.PK-1C strain was transformed with p416TEF-RtPSY1, pRS315GPD-$RtCRTI_{(A393T)}$ and either with pRS313TEF or pRS313TEF-tHMG1. Transformants were grown in minimal media supplemented with appropriate amino acids for overnight. And then reinoculated in fresh media till mid log phase. Yeast cells then harvested and dilution spotted on SD-ura-trp-his plates supplemented with appropriate amino acids at 0.2, 0.02, 0.002, 0.0002 O.D. Plates were incubated at 30° C. and photographs were taken after 3 days FIG. 12: Photomicrograph of spt15 mutant variants on pigmentation levels. S. cerevisiae was transformed with p416TEF-RtPSY1 and pRS315GPD-RtCRTI(A393T) and either with pRS313TEF-SPT15 mutated plasmids or with empty vector or wild type SPT15. Transformants were grown in minimal media supplemented with appropriate amino acids at 30° C. for overnight. And then re-inoculated in fresh media till mid log phase. Yeast cells then harvested and dilution spotted on SD-ura-trp-his plates supplemented with appropriate amino acids at 0.2, 0.02, 0.002, 0.0002 O.D Plates were incubated at 30° C. and then photographs were taken after 5 days.

Figure 13A:
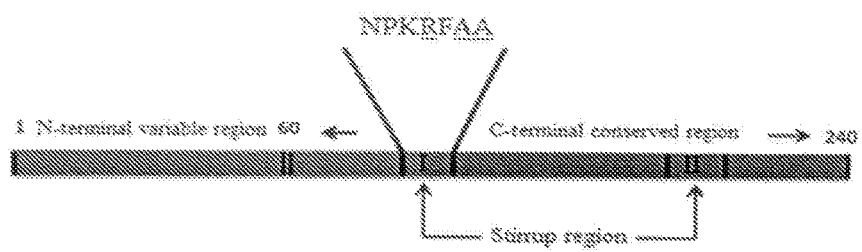
Figure 13B:
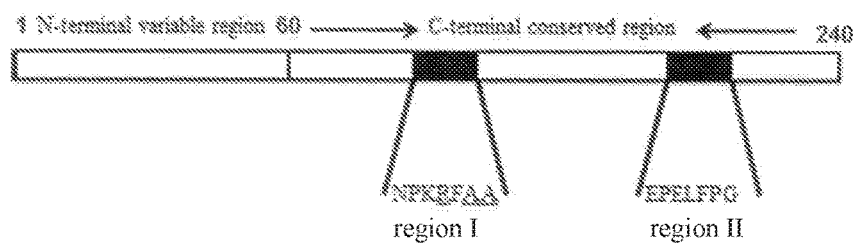

FIG. 13: Schematic representation of SPT15 domain structure depicted in FIG. 13A. Variable N-terminal 1-60 aa residues and conserved C-terminal 61-240 aa residues. C-terminal has two stirrup region (I and II depicted in FIG. 13B), present in C-terminal conserved region. Stirrup region I is proposed to interact with TFIIA. Mutated residues are underlined and are present in stirrup region I.

Figures 14A, 14B:
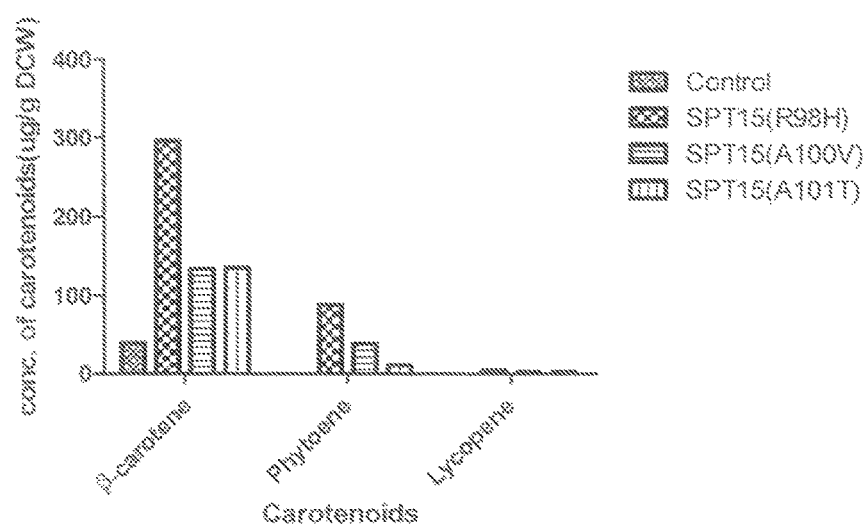

FIG. 14: Representation in tabular (FIG. 14A) and graphic (FIG. 14B) of chemical analysis of carotenoids produced by S. cerevisiae "V1 assay strain" containing SPT15 mutants. S. cerevisiae is transformed with p416TEF-RtPSY1+ pRS314GPD-RtCRTI(A393T)+pRS313TEF-SPT15 mutated plasmids-SPT15(R98H), SPT15(A100V), SPT15 (A101T), pRS313TEF-SPT15WT or pRS313TEF empty vector. Cultures were grown in 500 mL flasks containing 100 mL media for 5 days before extraction.

Figures 15A, 15B:
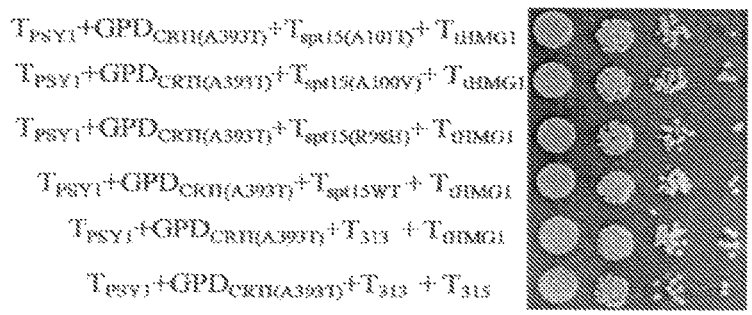

FIG. 15A is a photomicrograph showing the combinatorial effect of over expression of spt15 mutants and tHMG1 on the pigmentation levels of V1 assay strain and FIG. 15B depicts their chemical analysis by HPLC.

S. cerevisiae V1 assay strain was transformed with vector constructs pRS315TEF-tHMG1, pRS313TEF-spt15 mutants. (A) Transformants were grown in SD minimal media supplemented with appropriate amino acids at 30° C. for overnight, reinoculated in fresh media till mid log phase. Yeast cells then harvested and were dilution spotted at 0.2, 0.02, 0.002, 0.0002 O.D on SD-ura-leu-trp-his plates supplemented with appropriate amino acids respectively. Plates were incubated at 30° C. for 4 days and then photographs were taken. (B) The transformants were grown in 500 mL flasks containing 100 mL media for 3 days before extraction and HPLC analysis performed as described earlier.

Figure 16:
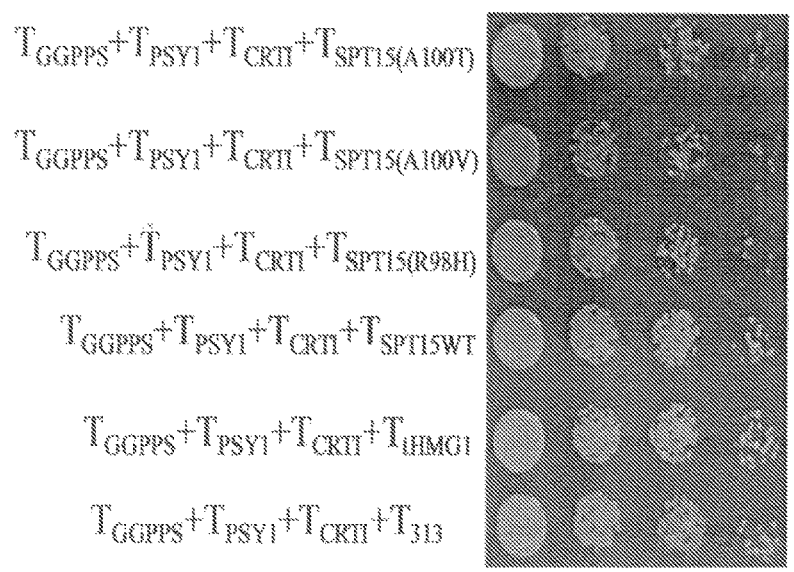

FIG. 16: Effect of spt15 mutants on pigmentation levels of transformants containing RtGGPPS under strong TEF promoter.

S. cerevisiae was transformed with vector constructs pRS315TEF-RtGGPPS, p416TEF-RtPSY1, pRS314TEF-RtCRTI. These transformants along with this constructs contains either empty vector pRS313TEF or pRS313TEF-tHMG1 or pRS313TEF-spt15 mutants. Transformants were grown in SD minimal media supplemented with appropriate amino acids at 30° C. for overnight. And then reinoculated in fresh media till mid log phase. Yeast cells then harvested and were dilution spotted at 0.2, 0.02, 0.002, 0.0002 O.D on SD-ura-leu-trp-his plates supplemented with appropriate amino acids respectively. Plates were incubated at 30° C. for 3 days and then photographs were taken.

Figure 17:
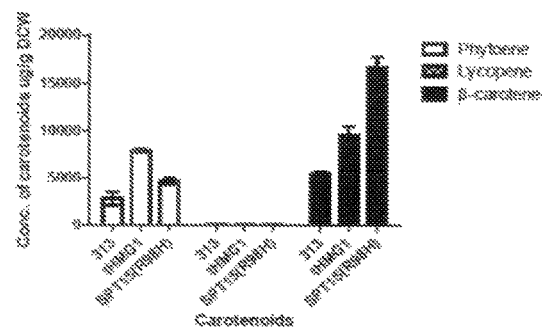

FIG. 17: Bar diagram representing the chemical analysis of spt15 mutants in strain background containing RtGGPPS under strong TEF promoter. Error Bar represents standard error mean of two independent flasks.

S. cerevisiae was transformed with vector constructs pRS315TEF-RtGGPPS, p416TEF-RtPSY1, pRS314TEF-RtCRTI. These transformants along with this constructs contains either empty vector pRS313TEF or pRS313TEF-tHMG1 or pRS313TEF-spt15 mutants. Cultures were grown in 500 mL flasks containing 100 mL media for 3 days before extraction.

Figure 18:
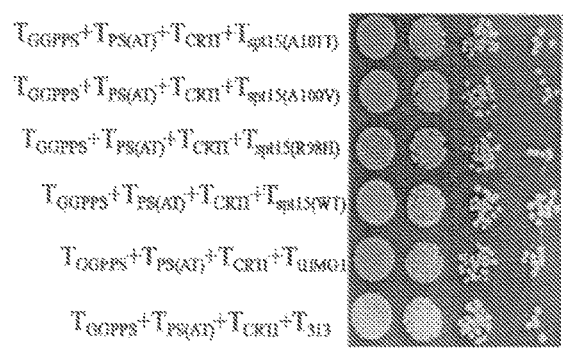

FIG. 18: Effect of spt15 mutants on pigmentation levels of Lycopene producing yeast S. cerevisiae was transformed with vector constructs pRS315TEF-RtGGPPS, p416TEF-AtPS, pRS314TEF-RtCRTI. These transformants along with this constructs contains either empty vector pRS313TEF or pRS313TEF-tHMG1 or pRS313TEF-spt15 mutants. Transformants were grown in SD minimal media supplemented with appropriate amino acids at 30° C. for overnight. And then reinoculated in fresh media till mid log phase. Yeast cells then harvested and were dilution spotted at 0.2, 0.02, 0.002, 0.0002 O.D on SD-ura-leu-trp-his plates supplemented with appropriate amino acids respectively. Plates were incubated at 30° C. for 3 days and then photographs were taken.

FIG. 19: Multiple sequence alignment of Phytoene dehydrogenase (RtCRTI) from different carotenoid producing fungi—*Rhodosporidium toruloides* (accession no. EMS24424.1), *Xanthophyllomyces dendrorhous* (accession noCAA75240.1), *Neurospora crassa* (accession no. XP_964713.1), *Aspergillus oryzae* (accession no. XP_001824518.2). Multiple sequence alignment was performed by Clustal W and Nterminal 1-56 amino acids which are present only in R. toruloides are shown by box.

Figure 20:
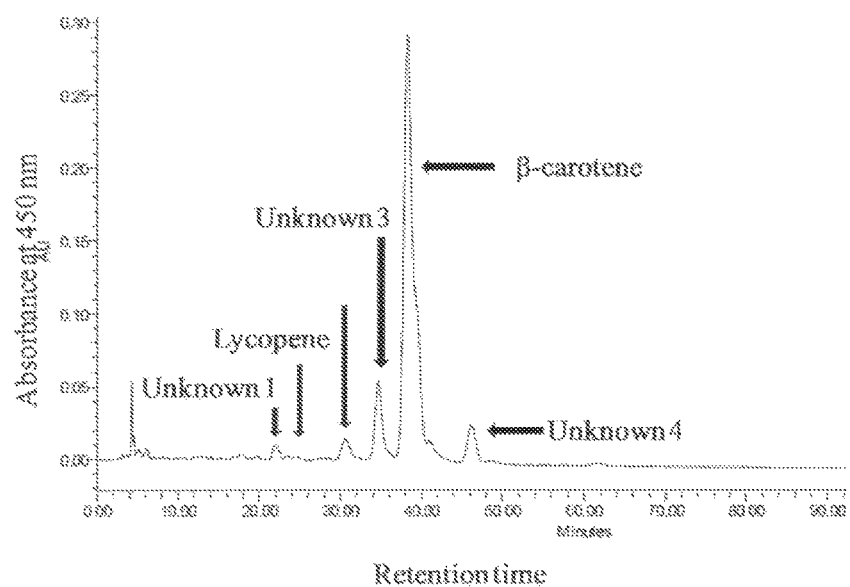

FIG. 20: HPLC chromatogram of strain ABC 276 containing $TEF_{RtGGPPS}+TEF_{RtPSY1}+TEF_{RtCRTI}$. It produces β-carotene as the major carotenoid. It also produces lycopene. The four unidentified peaks are labelled as unknown 1, 2, 3 and 4.

Figure 21:
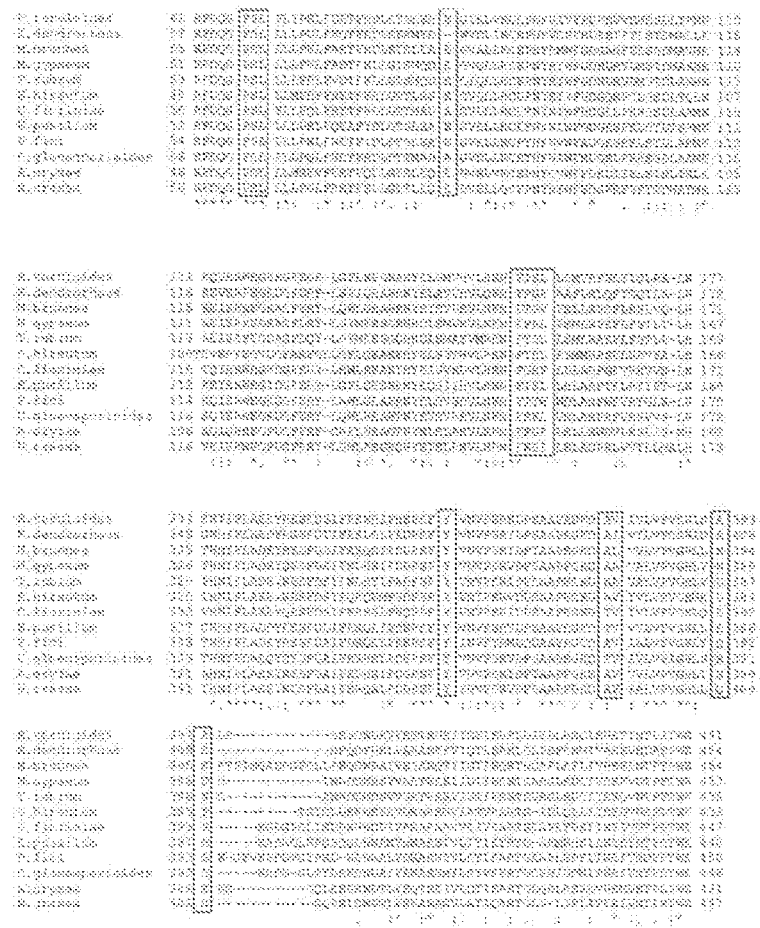
Figure 22:
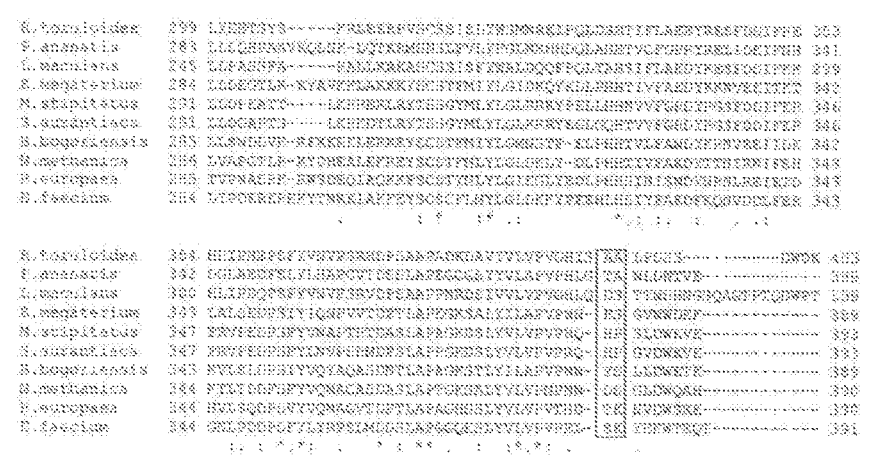

FIGS. 21 and 22: Multiple sequence alignment of phytoene dehydrogenase among fungi and bacteria. Multiple sequence alignment is performed by Clustal W and mutated residues of RtCRTI (A393 and A394) present in *R. toruloides* are shown by box.

Figure 23:
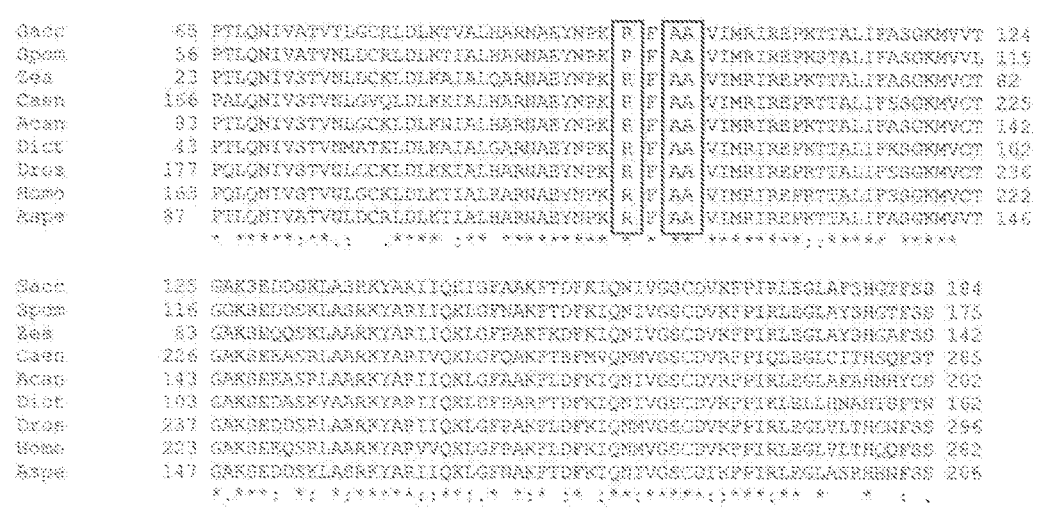

FIG. 23: Multiple sequence alignment of TATA binding protein (TBP) SPT15 genes from different species—*Saccharomyces cerevisiae* (accession no. P13393), *Schizosaccharomyces pombe* (accession no. NP_594566.1), *Zea mays* (accession no. NP_001105319.1), *Caenorhabditis elegans* (accession no. NP_498635.1), *Acanthamoeba castellanii* (accession no. XP_004338454.1), *Dictyostelium purpureum* (accession no. XP_003294984.1), *Drosophila melangaste* r (accession no. NP_523805.1), *Homo sapiens* (accession no. NP_003185.1) and *Aspergillus niger* (accession no. XP_001397705.2). Mutated residues R98, A100 and A101 were shown by red boxes and (numbered corresponding to sequence from R. toruloides) were shown by green box are part of N-terminal stirrup (96-101aa). Multiple sequence alignment was performed by ClustalW and conserved residues were shown by asterisk.

Figure 24:
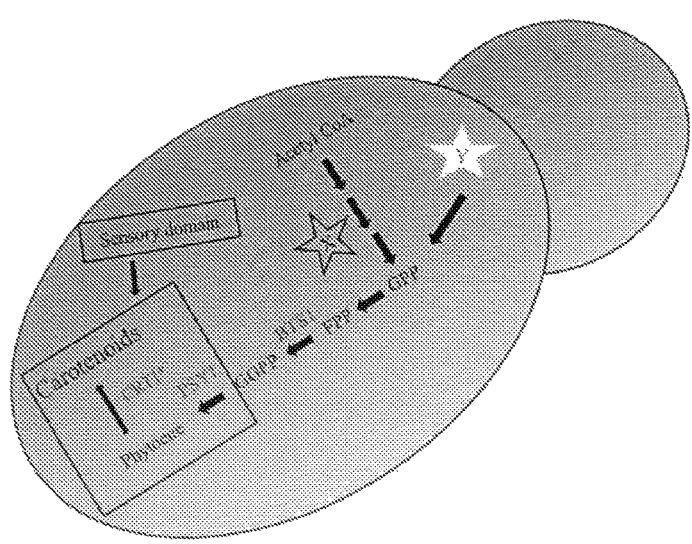

FIG. 24: Yeast model showing the isoprenoid pathway in S. cerevisiae which provides the precursor GGPP for synthesis of carotenoid. For functioning of carotenoid as sensory domain for identification of unknown flux determining genes X and Y, yeast is genetically modified by overexpression of RtPSY1 and mutated RtCRTI(A393T).

DETAILED DESCRIPTION OF THE INVENTION

Accordingly, the invention aims at increased isoprenoid production by carotenoid optimization.

Expression system for increased expression of isoprenoid by optimizing the carotenoid genes may be selected but not restricted to *S. cerevisiae* ABC276, *S. cerevisiae* BY4741, *S. cerevisiae* CEN.PK2 1C, *S. cerevisiae* CEN.PK2 1D, *S. cerevisiae* S288C, *S. cerevisiae* industrial strains, *Saccharomyces* spp., *Schizoaccharomyces* spp., *Pichia* spp., *Paffia* spp., *Kluyveromyces* spp., *Candida* spp., *Talaromyces* spp., *Brettanomyces* spp., *Pachysolen* spp., *Debaromyces* spp., *Hansula* spp.

The carotegenic gene for optimization may be geranylgeranyl diphosphate synthase (GGPPS), phytoene synthase (PSY1), conserved CRTI or mutated CRTI$_{A393T}$, BTS1 of *S. cerevisiae* and monofunctional phytoene synthase (lycopene synthase) of *Arabidopsis thaliana*.

The invention aims at increasing α-farnesene of the alternate isoprenoid pathway by expressing farnesene synthase gene of *Arabidopsos* or any plant in *S. cerevisiae*.

The carotogenic gene may be selected from red yeast which includes *Rhodosporidium* spp., *Rhodotorula* spp., *Sporidiobolus* spp., *Leucosporidium* spp., *Sporobolomyces* spp. and *Arabidopsis* spp. The *rhodosporidium* may be selected from *Rhodosporidium toruloides*, *Rhodosporidium diobovatum*, *Rhodosporidium sphaerocarpum*, *Rhodosporidium kratochilovae*.

The carotogenic gene may be selected from *Arabidopsis thaliana* or plants having 50% homology with carotenoid genes of *Arabidopsis*.

Codon optimization of the carotenoid genes of the *Rhodosporidium* spp. is done, using EnCor Biotechnology Inc. software and cloned in yeast centromeric plasmids. The yeast centromeric plasmids p416TEF, pRS313TEF, pRS314TEF, pRS315TEF as well as the same series with the CYC promoter were used for cloning and expression of carotenogenic genes.

The promoter may be CYC, TEF, GPD or TDH or a combination of these. The promoter may be conserved or mutated or a combination.

Further for the identification and reconstruction of the core carotenoid biosynthetic pathway, genes of *Rhodosporidium toruloides* were cloned into *Saccharomyces cerevisiae*, the RtGGPPS, RtPSY1 and RtCRTI cDNAs were cloned in yeast single copy (CEN) expression vectors under the TEF promoter and CYC as terminator. These genes were cloned in pRS315TEF, p416TEF and pRS314TEF respectively. These constructs were transformed in *S. cerevisiae* ABC276 strain and transformants were selected on SD-ura-leu-trp plates. HPLC analysis showed that expression of RtGGPPS, RtPSY1 and RtCRTI were able to produce β-carotene (5105.08 µg/g DCW), phytoene (2727.95 µg/g DCW) and negligible amounts of lycopene (95.47 µg/g DCW) based on comparison with retention time of available authentic carotenoid standards.

For the identification of V1 assay strain the replacement of the RtGGPPS with the *S. cerevisiae* BTS1 was carried out.

Further, gene mutations of SPT15 gene were carried out to increase flux through the isoprenoid pathway and to isolate mutants showing increase flux in the isoprenoid pathway.

For overexpression of truncated HMG1 CoA reductase (tHMG1), the C-terminal catalytic region (1575 bp) was amplified from *S. cerevisiae* genomic DNA using tHMG1-FP and tHMG1-RP and the amplified tHMG1.

Plasmid vectors, cloning of genes and preparation of transformants are according to the method described in standard biotechnology techniques.

The method of increased isoprenoid flux in *Saccharomyces* comprises of the following steps:
Codon optimization of the carotenoid genes of the *Rhodosporidium* spp. as per codon usage frequency of host strain.
Optimization of the promotor for the expression of the carotenoid genes.
Overexpression of HMG1 with or without truncated HMG1.
Overexpression of upc2 with and without mutation
Down regulation of ERG9

The method of increased isoprenoid flux in *Saccharomyces* comprises of the following steps:
Codon optimization of the carotenoid genes of the *Rhodosporidium* spp or a conserved gene of *Saccharomyces* BTS1 or a combination as per codon usage frequency of host strain.
Optimization of the promotor for the expression of the carotenoid genes and identification of the V1 assay strain.
Overexpression of HMG1 with or without truncated HMG1.
Overexpression of upc2 with and without mutation
Down regulation of ERG9

The method of increased isoprenoid flux in *Saccharomyces* comprises of the following steps:
Codon optimization of the carotenoid genes of the *Rhodosporidium* spp. or a conserved gene of *Saccharomyces* BTS1 or a combination as per codon usage frequency of host strain.
Optimization of the promotor for the expression of the carotenoid genes and identification of the V1 assay strain.
Cloning of native or mutant spt15 for increased flux in isoprenoid.
Overexpression of HMG1 with or without truncated HMG1.
Overexpression of upc2 with and without mutation.
Down regulation of ERG9.

The method of increased isoprenoid flux in *Saccharomyces* comprises of the following steps:
Codon optimization of the carotenoid genes of the *Rhodosporidium* spp. or a conserved gene of *Saccharomyces* BTS1 or a combination as per codon usage frequency of host strain.
Optimization of the promotor for the expression of the carotenoid genes and identification of the V1 assay strain.
Cloning of mutant phytoene dehydrogenase (RtCRTI) for increased flux in isoprenoid.
Overexpression of HMG1 with or without truncated HMG1
Overexpression of upc2 with and without mutation
Down regulation of ERG9

EXAMPLES

The following examples are for the purpose of illustration of the invention and are not intended in any way to limit the scope of the invention.

Example 1: Plasmid Vectors, Cloning of Genes and Transformation

The yeast centromeric plasmids p416TEF, pRS313TEF, pRS314TEF, pRS315TEF as well as the same series with the CYC promoter were used for cloning and expression of carotenogenic genes. pRS313TEF, pRS314TEF and pRS315TEF were constructed by excising the MCS and TEF promoter regions from p416TEF plasmid and cloning into pRS313, pRS314 and pRS315 respectively. The genes for GGPP synthase (RtGGPPS), Phytoene synthase (RtPSY1) and Phytoene dehyrogenase (RtCRTI) of *R. toruloides* were Codon optimized by using EnCor Biotechnology Inc. software and custom synthesized by GenScript USA Inc. and cloned in pRS315TEF, p416TEF, pRS314TEF respectively. RtGGPPS was cloned at the XbaI and BamHI sites of pRS315TEF to construct pRS315TEF-RtGGPPS, RtPSY1 was cloned at BamHI and XhoI sites of p416TEF to yield p416TEF-RtPSY1 while RtCRTI is cloned at BamHI and SalI site to construct pRS314TEF-RtCRTI. For overexpression of truncated HMG1 CoA reductase (tHMG1), the C-terminal catalytic region (1575 bp) was amplified from *S. cerevisiae* genomic DNA using tHMG1-FP and tHMG1-RP and the amplified PCR product was cloned at the BamHI and XmaI sites of pRS313TEF to construct pRS313TEF-tHMG1. For construction of p416CYC-RtPSY1, p416TEF-RtPSY1 is digested with SacI and BamHI to excise the TEF promoter and ligated with SacI and BamHI digested CYC1 promoter from p414CYC1 vector. pRS314CYC-RtCRTI was constructed similarly. pRS315CYC-RtGGPPS was constructed from pRS315TEF-RtGGPPS by digesting with XbaI and SacI to excise the TEF promoter and ligated with XbaI and SacI digested CYC1 promoter of p414CYC1 vector. SPT15 was amplified from *S. cerevisiae* ABC 276 strain by using the forward and reverse primers and cloned in the BamHI and XhoI sites of pRS313TEF. The cDNA for α-Farnesene synthase (Locus AT4G16740 and clone no. U88221) from *A. thaliana* was obtained from TAIR database, USA. It was PCR amplified and subcloned in XbaI and BamHI site of pRS315TEF to make the construct pRS315TEF-AtFS. The cDNA for phytoene synthase from *A. thaliana* (Locus AT5G17320) was obtained from TAIR database, USA. It was PCR amplified and subcloned in BamHI and XhoI site of p416TEF to make construct p416TEF-AtPS. All these constructs were transformed into *S. cerevisiae* strain (ABC276) by Lithium acetate method (Sambrook et al., 1989). All the primers and plasmids constructed to perform the invention are indicated in Table 1 and Table 2 below.

TABLE 1

List of oligonucleotides and their sequences

| Oligomer | Sequence (5'-3') |
|---|---|
| tHMG1 F | GATCGCGGATCCATGGACCAATTGGTGAAAACTGAAG |
| tHMG1 R | CATGCGCCCGGGTTAGGATTTAATGCAGGTGACG |
| SPT15 F | GATCGCGGATCCATGGCCGATGAGGAACGTTTAAAG |
| SPT15 R | CATGCGCTCGAGTCACATTTTTCTAAATTCAC |
| AtFS F | GACGTTCTAGAATGCCTAAACGACAGGCTCAAC |
| AtFS R | GGCTCGGATCCTTAATTGAGTGGAAGAGGGTGG |
| AtPS F | ACGCATGGATCCATGTCTTCAAGCTTAGTAGCAAG |
| AtPS R | GGTCATATTTCTACTGGTTTGCCATCTTCTTCTG |

TABLE 2

Lists of plasmid used

| Plasmids | Relevant features |
|---|---|
| p416TEF-PSY1 | p416 TEFp-PSY1-CYC1t |
| pRS314TEF-CRTI | pRS314 TEFp-CRTI-CYC1t |
| pRS315TEF-RtGGPPS | pRS315 TEFp-GGPPS-CYC1t |

TABLE 2-continued

Lists of plasmid used

| Plasmids | Relevant features |
|---|---|
| pRS314TEF-RtCRTI(A393T) | pRS314TEFp-CRTI$_{A393T}$-CYC1t |
| pRS313TEF-tHMG1 | pRS313 TEFp-tHMG1-CYC1t |
| pRS313TEF-SPT15 | pRS313 TEFp-SPT15-CYC1t |
| p416CYC-RtPSY1 | p416 CYC1p-PSY1-CYC1t |
| pRS314CYC-RtCRTI | pRS314 CYC1p-CRTI-CYC1t |
| pRS315CYC-RtGGPPS | pRS315 CYC1p-GGPPS-CYC1t |
| pRS314CYC-RtCRTI(A393T) | pRS314CYCp-CRTI$_{A393T}$-CYC1t |
| pRS314GPD-RtCRTI(A393T) | pRS314GPDp-CRTI$_{A393T}$-CYC1t |
| pRS313TEF-SPT15(R98H) | pRS313 TEFp-SPT15$_{R98H}$-CYC1t |
| pRS313TEF-SPT15(A100T) | pRS313 TEFp-SPT15$_{A100T}$-CYC1t |
| pRS313TEF-SPT15(A101V) | pRS313 TEFp-SPT15$_{A101V}$-CYC1t |
| pRS315TEF-AtFS | pRS315 TEFp-AtFS-CYC1t |
| p416TEF-AtPS | p416TEFp-AtPS-CYC1t |

Strains and Media:

*Escherichia coli* strain DH5α was used as cloning host. *S. cerevisiae* strains CEN, PK2-1C-MAT α, ura 3-52, trp 1-289, leu2-3_112, his3Δ1, MAL 2-8$^c$, SUC2 and *S. cerevisiae* strain (ABC 276) which is a derivative of S288c strain with genotype MAT α ura 3-52 leu2Δ1 his3Δ200 trp1 lys2-801 GAL are used in this study. The strain was derived from tetrad analysis of diploids made between BJ5418 and BJ5458 strains which are obtained from the Beth Joan laboratory. These strains were maintained on yeast extract, peptone and dextrose (YPD) media. For culturing yeast-synthetic defined media (SD) containing yeast nitrogen base (YNB) without ammonium sulphate 0.15% (w/v) and amino acids supplemented with appropriate amino acids and 0.5% (w/v) ammonium sulphate and 2% (w/v) D-glucose is used.

Extraction of Carotenoids and Analysis by HPLC:

Extraction of carotenoids was carried out earlier (Moline et al., 2012) with some modifications. Essentially, yeast cells were grown in 100 mL SD media supplemented with appropriate amino acids and grown at 30° C. with shaking (250 rpm). After five days, cells were harvested and washed with deionized water and kept at −20° C. To the frozen pellet was added 3 mL of Dimethyl sulphoxide (DMSO), vortexed for 1 min and incubated at 55° C. in the water bath for 1 hour. 1 g 0.50-0.75 mm glass beads were added, and cells broken using glass bead beater. Cells were centrifuged to remove the cell debris. Acetone was added to the pellet, vortexed and centrifuged and the process repeated till the pellet becomes colorless. The acetone and DMSO fractions were mixed with an equal amount of Hexane. The colored hexane layer was collected after separation of two layers. The hexane layer was washed with distilled water and then with brine solution twice. The colored hexane layer was collected. The solvent was evaporated under rotary evaporator to dryness in dim light and was dissolved in 1 mL hexane for analysis by high performance liquid chromatography (HPLC). HPLC separation and quantification was performed on Waters system using $C_{18}$-5 μm intersil ODS-P, 250×4.6 mm column (LCGC) using solvent acetonitrile:methanol:2-propanol (85:10:5 v/v) with flow rate 1 mL/min at 32° C. Separated carotenoids were detected by photodiode array detector. Quantification of carotenoids was done by using standard curve prepared for β-carotene, lycopene and phytoene. Standards for β-carotene and lycopene were obtained from Sigma Aldrich, India and phytoene were obtained from Carote Nature GmbH, Switzerland. Standards of β-carotene, lycopene and phytoene were dissolved in hexane and the concentration of β-carotene, lycopene were calculated using extinction coefficient ($A^{1\%}$) of 2590, 3450 in hexane respectively and the concentration of phytoene was calculated using extinction coefficient ($A^{1\%}$) of 750 in hexane/2% $CH_2Cl_2$. Concentration of β-carotene, lycopene and phytoene in samples were expressed in μg per g dry cell weight (μg/g DCW). For calculating the dry cell weight, samples were kept at 80° C. in an oven for 48 hours and their dried weights were measured.

In Vitro Mutagenesis:

Random mutagenesis in vitro was performed on the purified plasmids by Hydroxlyamine as described earlier (Rose and Fink 1987). The average number of mutations obtained from hydroxylamine mutagenesis was approximately 1 per kb.

Dilution Spotting for Growth and Colour Visualization:

Yeast cells were grown overnight in SD media supplemented with appropriate amino acids, re-inoculated in fresh media at 0.1 O.D and grown to 0.6-0.8 O.D. Yeast cells were harvested, washed with deionized water and re-suspended at different dilutions. 10 μl of different dilutions at 0.2, 0.02, 0.002 and 0.0002 O.D are spotted on SD plate supplemented with appropriate amino acids.

Modelling of Phytoene Dehydrogenase:

Modelling of phytoene dehydrogenase of *R. toruloides* was performed using Phyre2 (http://www.sbg.bio.ic.ac.uk/phyre2). Phytoene dehydrogenase from *Pantoea ananatis* (PDB Id-4DGK) was used as a template for modelling.

Identification and Quantification of α-Farnesene:

*S. cerevisiae* ABC 276 was transformed with pRS315TEF-AtFS. Transformants were grown in SD media containing appropriate amino acids. Secondary culture was grown at 0.05 O.D and when O.D reaches to 0.6-0.8, culture was overlaid with 10% dodecane. After 48 hrs, the dodecane phase of the two-phase culture was collected by centrifugation of culture at 6000 rpm for 5 minutes. 1 uL of dodecane phase was subjected to GC-FID analysis. Samples were injected at a split ratio of 1:10. The oven temperature was initially held at 80° C. for 1 min and was increased at a rate of 10° C./min to 250° C. where it was held for 1 minute. Carrier gas was nitrogen. And the temperature of detector was maintained at 260° C. All the conditions used for GC analysis was followed from Wang et al., 2011. Standard curve of trans β Farnesene was prepared using GC-FID. Trans β-Farnesene (Cat. 73492) from Sigma Aldrich, India was used as standard.

Sequence Accession Numbers:

The codon optimized and custom synthesized genes—GGPP synthase (RtGGPPS), Phytoene synthase (RtPSY1) and phytoene dehydrogenase (RtCRTI) were submitted to Genbank database and have the following accession numbers KU041640, KU041641 and KU041642 respectively.

Example 2: Identification and Reconstruction of the Core Carotenoid Biosynthetic Pathway Genes of *Rhodosporidium toruloides* into *Saccharomyces cerevisiae*

As the red yeasts that includes *R. toruloides* are amongst the highest producers of β-carotene, the core carotenoid pathway of *R. toruloides* was reconstructed in *S. cerevisiae*. The core pathway involves three enzymes-GGPP synthase, Phytoene synthase and Phytoene dehydrogenase. Expression of these genes has been predicted to produce β-carotene in addition to torulene and γ-carotene (FIG. 1).

Using the genome sequence information from the genome sequence of this yeast that we recently described along with others (Kumar et.al, 2012; Zhu et.al., 2012) identified the putative genes that code for Geranylgeranyl diphosphate synthase (RtGGPPS), Phytoene synthase (RtPSY1) and Phytoene dehydrogenase (RtCRT1). The putative gene and protein sequences were retrieved and genes with ORF numbers as RtGGPPS (RHTO_02504), Phytoene synthase (RHTO_04605) and Phytoene dehydrogenase (RHTO_04602) were obtained.

The GGPP synthase gene encodes a protein of 359 aa with 62% similarity (E-value 2e-112) to GGPPS from *X. dendrorhous*.

The Phytoene synthase gene encodes a protein of 612 aa with 45% similarity (E-value 4e-76) to the phytoene synthase of *X. dendrorhous*.

The predicted Phytoene dehydrogenase of *R. toruloides* is 610 aa in length (suppl Table 1)

| Enzymes | No. of introns | No. of Exons | Length | BLAST with *X. dendrorhous* E-value Similarity | BLAST with *N. crassa* E-value Similarity |
|---|---|---|---|---|---|
| GGPP synthase (RtGGPPS) | 07 | 08 | 359aa | 2e-112 62% | 2e-116 73% |
| Phytoene synthase (RtPSY1) | 07 | 08 | 612aa | 4e-76 45% | 2e-110 54% |
| Phytoene dehydrogenase (RtCRTI) | 09 | 10 | 610aa | 2e-176 68% | 3e-174 70% |

However, the protein appeared to have an extra N-terminal of 56 amino acids as compared to the phytoene dehydrogenase of *X. dendrorhous* and other phytoene dehydrogenases (Suppl FIG. 19). It thus appeared that this extra N-terminal may be a consequence of a mis-annotation of the start site, and we therefore only considered the genic region that corresponded to the remaining 554 aa. The protein has 68% similarity (E-value 2e-176) to the Phytoene dehydrogenase from *X. dendrorhous*.

As the genes contained multiple introns, and as *R. toruloides* has a high G-C content compared to *S. cerevisiae*, we opted to custom synthesize the cDNAs for these genes after codon optimization for expression in *S. cerevisiae*.

The RtGGPPS, RtPSY1 and RtCRTI cDNAs were cloned in yeast single copy (CEN) expression vectors under the TEF promoter and CYC as terminator. These genes were cloned in pRS315TEF, p416TEF and pRS314TEF respectively. These constructs were transformed in *S. cerevisiae* ABC276 strain and transformants were selected on SD-ura-leu-trp plates. Expression of these genes produced a deep orange color in yeast (FIGS. 2A (2*a* and 2*b*)).

HPLC analysis showed that expression of RtGGPPS, RtPSY1 and RtCRTI were able to produce β-carotene (5105.08 μg/g DCW), phytoene (2727.95 μg/g DCW) and negligible amounts of lycopene (95.47 μg/g DCW) based on comparison with retention time of available authentic carotenoid standards (FIG. 2B). We have also obtained four unknown peaks in HPLC chromatogram whose identity yet to be determined (suppl FIG. 22). In previous studies in which CrtYB (phytoene synthase)/CrtI (phytoene dehydrogenase)/CrtE (GGPP synthase)(carotenogenic) genes of *X. dendrorhous* (in episomal plasmids) were expressed in *S. cerevisiae*, high levels of phytoene, lycopene were observed (Veerwal et.al, 2007) while low levels of β-carotene were detected. In contrast, using the *R. toruloides* genes we observed β-carotene as the major fraction of total carotenoids with very low amount of phytoene and lycopene, although a similar deep orange colored colony was observed. This preliminary analysis suggested that opting for genes from R. toruloides was a preferred option since it led to low levels of intermediates i.e. phytoene and lycopene, relative to β-carotene.

Example 3: Effect of Different Promoter Combinations with RtGGPPS, RtPSY1 and RtCRTI on Pigmentation Levels To use colour of carotenoid as a visual screen for increasing the flux in the isoprenoid pathway, we needed a strain that would produce low level of carotenoids (hence less colour), but would show increased pigmentation if the flux in the pathway was be increased. To set about constructing such a strain in S. cerevisiae, RtGGPPS, RtPSY1, RtCRTI was cloned and expressed under the weak CYC promoter (and CYC terminator). A S. cerevisiae strain was separately transformed with different TEF and CYC promoter combination of RtGGPPS, RtPSY1, RtCRTI genes constructs. The transformants were spotted and a wide variation in color was observed (FIG. 3). The strain combinations that produced more color were those that contained phytoene dehydrogenase (RtCRTI) expressed under a strong constitutive promoter. These strain combinations were: $TEF_{GGPPS}+TEF_{PSY1}+TEF_{CRTI}$, $CYC_{GGPPS}+CYC_{PSY1}+TEF_{CRTI}$, $CYC_{GGPPS}+TEF_{PSY1}+TEF_{CRTI}$ and $TEF_{GGPPS}+CYC_{PSP1}+TEF_{CRTI}$. Conversely, the strain combinations that produced the lowest color were when RtCRTI was expressed under the weak promoter. These combination strains are as $CYC_{GGPPS}+CYC_{CPS1}+CYC_{CRTI}$, $TEF_{GGPPS}+TEF_{PSY1}+CYC_{CRTI}$, $TEF_{GGPPS}+CYC_{PSY1}+CYC_{CRTI}$ and $CYC_{GGPPS}+TEF_{PSY1}+CYC_{CRTI}$. As we required low carotenoid producing strains, these latter low carotenoid producing combination strains were candidates that could be used as background strains for genetic assay for increasing flux in the isoprenoid pathway.

Example 4: Increasing the Flux in the Isoprenoid Pathway by Over Expression of tHMG1 Fails to Increase Pigmentation Levels and Carotenoid Levels in the Different Strain Background: RtCRTI as the Possible Rate Limiting Step To check whether the low color producing strains could be used for identification of regulatory/flux determining genes of the isoprenoid pathway, the truncated catalytic domain of HMG1 (tHMG1) which is known to increase the flux in the pathway, was overexpressed in these different promoter combination strains. The overexpression of tHMG1 in these different strains did not show an increase in color despite an expected increase in flux in the isoprenoid pathway (FIG. 4). Strain combinations such as $CYC_{GPPS}+CYC_{PSY1}+CYC_{CRTI}$, $TEF_{GGPPS}+TEF_{PSY1}+CYC_{CRTI}$, $TEF_{GGPPS}+CYC_{PSY1}+CYC_{CRTI}$ and $CYC_{GPPS}+TEF_{PSY1}+CYC_{CRTI}$ show slight decrease in color with overexpression of tHMG1. The maximum decrease in color was observed in strain combination $TEF_{GGPPS}+TEF_{PSY1}+TEF_{CRTI}$ and $TEF_{GGPPS}+CYC_{PSY1}+TEF_{CRTI}$ with overexpression of tHMG1. There is approximately same color with and without overexpression of tHMG1 in strain combination—$CYC_{GPPS}+CYC_{PSY1}+TEF_{CRTI}$, $CYC_{GGPPS}+TEF_{PSY1}+TEF_{CRTI}$. One possibility for decrease in color in strain combinations with overexpression of tHMG1, there is much more accumulation of pathway intermediates such as colourless phytoene as compared to much more production of β-carotene in these strain combinations and it could occur if phytoene dehydrogenase is rate limiting.

HPLC analysis of $TEF_{GGPPS}+TEF_{PSY1}+TEF_{CRTI}$ strain containing either an empty vector or tHMG1 was carried out. Comparison of strains with and without over expression of tHMG1 revealed that with over expression of tHMG1, there is 2.84 fold increase in levels of phytoene, but only 1.77 fold increase in the levels of β-carotene suggesting that the dehydrogenation/desaturation of phytoene is limiting is provided in table 3.

TABLE 3

Yield of carotenoids in different background strains.

| Sr. no. | Sample ID | β-carotene conc. (ug/g DCW) | Lycopene conc. (ug/g DCW) | Phytoene conc. (ug/g DCW) |
|---|---|---|---|---|
| 1. | TGGPPS + TPSY1 + TCRTI | 5105.08 | 95.47 | 2727.95 |
| 2. | TGGPPS + TPSY1 + TCRTI + pRS313TEF | 5444.56 | 34.63 | 2770.32 |
| 3. | TGGPPS + TPSY1 + TCRTI + TtHMG1 | 9673.1 | 60.97 | 7890.52 |
| 4. | TGGPPS + TPSY1 + CCRTI | 127.62 | 25.93 | 13357.80 |
| 5. | TGGPPS + TPSY1 + CCRTI (A393T) | 532.87 | 29.73 | 2896.80 |
| 6. | TGGPPS + TPSY1 + TCRTI(A393T) + pRS313TEF | 14727.03 | 95.60 | 6398.22 |
| 7. | TGGPPS + TPSY1 + TCRTI(A393T) + TtHMG1 | 11475.52 | 51.70 | 8409.68 |
| 8. | TPSY1 + GPDCRTI(A393T) + pRS313TEF | 39.04 | ND | ND |
| 9. | TPSY1 + GPDCRTI(A393T) + TtHMG1 | 144.08 | 5.47 | 185.36 |

Example 5: Isolation of Catalytically Efficient Mutants of Phytoene Dehydrogenase by the Pigmentation Screen To increase phytoene desaturation, one possible approach that has been tried earlier (Verwaal et.al., 2006) is to increase the expression levels of RtCRTI either by increasing the copy number of the plasmid, or the promoter strength driving expression. However, as both these approaches tends to place a higher load on the cells capabilities, it was attempted to isolate more active mutants of the rate limiting phytoene dehydrogenase (RtCRTI). In vitro random mutagenesis of phytoene dehydrogenase in the plasmid pRS314CYC-RtCRTI (where Phytoene dehydrogenase was under the weak CYC promoter) was carried out. The library of CRTI mutants in this plasmid was directly transformed into the S. cerevisiae strain with $TEF_{GGPPS}+TEF_{PSY1}$ plasmids. Transformants were selected on SD-leu-ura-trp plates and screened on the basis of increased color as compared to the color of control strain with $TEF_{GGPPS}+TEF_{PSY1}+CYC_{CRTI}$. A total of six mutants was initially picked up, and after isolation of the plasmids, and amplification through E. coli, and retransformation, three mutants could be confirmed to confer increase pigmentation to the strains. The plasmids were subjected to sequencing. Two mutants were found to have an Alanine 393 to Threonine mutation in the coding sequence, while one mutant was found to have an Alanine394 to Glycine mutation. Interestingly, all three mutants clustered in the same region. These mutants produce more color as compared to control S. cerevisiae strain with $TEF_{GGPPS}+TEF_{PSY1}+CYC_{CRTI}$ but less color as compared to S. cerevisiae strain with $TEF_{GGPPS}+TEF_{PSY1}+TEF_{CRTI}$ suggesting more active than wild type RtCRTI (FIG. 5).

Sequence analysis and conservation pattern of the Ala393 and Ala394 residues of phytoene dehydrogenase of R. toruloides with similar enzymes of other fungi and bacteria revealed that the residues were not conserved among bacteria and fungi (Suppl FIGS. S2a and S2b). Interestingly, the carotenoid producing bacteria Pantoea annatis has a threonine at position 393 and an alanine at 394. Therefore, the mutant Ala393Thr have identical residues at 393 and 394 position as the phytoene dehydrogenase from P. annatis.

The phytoene dehydrogenase of R. toruloides was modeled on the crystal structure of Pantoea ananatis (PDB Id-4DGK). The residues Ala393 and Ala394 were, however, not present in active site. To see whether mutation has increased activity of CRTI, we quantitated carotenoids by HPLC. HPLC analysis showed that there is 4.6 fold decrease in levels of phytoene and 4.17 fold increase in β-carotene levels with the mutant enzyme as compared to the wild type enzyme (FIG. 6).

Example 6: A Pigmentation-Based Phenotypic Screen that Responds to Increased Flux in the Isoprenoid Pathway as Seen by Overexpression of tHMG1

Since the RtCRTI enzyme was rate limiting with overexpression of tHMG1, the $RtCRTI_{A393T}$ mutant was included to optimize the genetic screen for increase in color with increase in the flux (with overexpression of tHMG1). The pRS313TEF-tHMG1 plasmid was transformed in different combination strain of $pRS314CYC-RtCRTIA_{A393T}$.

However, surprisingly, none of the combinations showed expected increase in color with tHMG1 (FIG. 7). It could be due to continued accumulation of phytoene even with mutant phytoene dehydrogenase since a weaker promoter of $CRTI_{A393T}$ was used. Therefore mutant of $RtCRTI_{A393T}$ was expressed under the strong TEF promoter, however, here too, only marginal increase in color was observed with over expression of tHMG1 in strain combination $CYC_{GPPS}+TEF_{PSY1}+TEF_{CRTI(A393T)}$ (FIG. 8). It suggested that phytoene was still accumulating and its desaturation is still limiting despite use of strong promoter and active mutant of phytoene dehydrogenase. HPLC analysis of $TEF_{GGPPS}+TEF_{PSY1}+TEF_{CRTI(A393T)}$ combination showed that with over expression of tHMG1, there is 1.31 fold increase in production of phytoene, but β-carotene levels remains approximately the same. It was therefore considered necessary to further decrease the accumulation level of phytoene to make an effective genetic screen. This was attempted by decreasing the expression of the upstream gene, GGPP synthase. However, as even the CTT combination give only marginal increase in color, we considered it possible that the RtGGPPS was too efficient and must be replaced by a less efficient enzyme and thus attempted to decrease the phytoene levels by using S. cerevisiae GGPPS (BTS1) from S. cerevisiae native promoter (BTS1) in place of RtGGPPS. Using this combination of native BTS1 along with $RtCRTI_{A393T}$ under the stronger GPD promoter ($pRS315GPD-RtCRTI_{A393T}$), pRS314TEF-RtPSY1 and pRS313TEF-tHMG1 (FIG. 9), we could finally observe the desired increase in color with over-expression of tHMG1. HPLC analysis of V1 assay strain suggests that this strain produces only β-carotene without overexpression of tHMG1 as phytoene and lycopene are not detected (FIG. 10). Therefore, this strain combination that we refer to here as the "V1 assay strain" seems suitable as a visual genetic screen for isolating new genes and mutants that increase the flux in isoprenoid pathway.

To determine whether the combination of plasmids used in the V1 assay strain behaved similarly in other S. cerevisiae strain backgrounds, industrially important strain of S. cerevisiae-CEN.PK-1C was examined and transformed it with V1 assay combination plasmids along with either pRS313TEF or pRS313TEF-tHMG1. Results (FIG. 11) indicated a similar increase in colour with over expression of tHMG1 suggesting that the assay combination can be generalized for other S. cerevisiae backgrounds.

Figure 12:
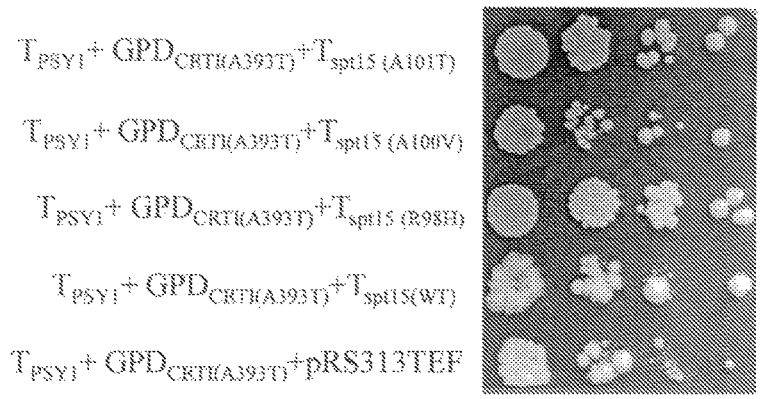

Example 7: Isolation of Mutants in SPT15, the Global TATA Binding Protein Using the Phenotypic Pigmentation Screen Reveals Mutations in SPT15 that can Significantly Increase the Flux in the Isoprenoid Pathway To evaluate the screen for its ability to pickup new genes it was decided to examine if mutants in a global TATA binding protein (TBP), SPT15 could be isolated that could result in increased flux in isoprenoid pathway. SPT15 was cloned downstream of the TEF and subjected to random in vitro mutagenesis with hydroxylamine. The SPT15 mutant library was transformed into the yeast strain bearing the carotenogenic plasmids developed as the host for the phenotypic screen as described above. A total of 6 colonies were initially selected on the basis of enhanced color as compared to control background strain. Plasmids were isolated from these strains, purified and amplified through E. coli, retransformed into the yeast strain and spotted to confirm the phenotype (FIG. 12). Three of these mutants from independent mutant stocks were found to display increased pigmentation. Sequencing revealed that these mutants carried mutations Arg98His, Ala100Val and Ala101Thr respectively. Mutant Arg98His showed significant enhancement in color as compared to control background strain. Mutant Arg98His is obtained twice from two independent mutant stocks. Sequence analysis revealed that these residues are present in the C-terminal region and conserved across species (Chasman et al., 1993)

To confirm the increased flux through the pathway, the carotenoid levels of the three mutants with a control strain was compared, and also with strains bearing the wild type SPT15. It was observed that the R98H mutant showed a greater than 7-fold increase in β-carotene with only a marginal increase in phytoene. In contrast the A100V and A101T mutants showed an approximately 3-fold increase in β-carotene and a significant decrease in phytoene levels (FIG. 14A and B).

It also examined whether combining the tHMG1 along with the spt15 mutants could lead to further enhancement in carotenoid levels. tHMG1 was combined with $spt15_{(A101T)}$ in the V1 assay strain but could not find any further increase with this combination (FIG. 15A and B).

Strains with Non-Limiting Concentrations of GGPP also Show Elevated Levels of Carotenoids with the spt15 Mutants:

The V1 assay strain was designed for the isolation of mutants that increase the flux in the isoprenoid pathway.

However, considering that the strain was very limiting for GGPP (since it carried the native *S. cerevisiae* GGPP synthase under its own promoter), it was if the mutants isolated through the screen would also be able to confer increased flux under conditions where GGPP was not limiting. The transformed spt15 mutants in *S. cerevisiae* strain having RtGGPPS, RtPSY1, RtCRTI genes were expressed under the strong TEF promoter (and CYC terminator). These transformants were dilution spotted on SD plates. It has been observed that in this strain background, when tHMG1 is over expressed, the colour of the strain decreases despite the increase in the flux in the isoprenoid pathway. However, in the present study it was observed with over expression of spt15 mutants the colour did not decrease but rather a marginal increase in colour was observed with over expression of spt15 mutants (FIG. 16). To further confirm the increase in carotenoid production in this strain with over expression of spt15 mutants, we carried out HPLC analysis of strain containing pRS315TEF-RtGGPPS, p416TEF-RtPSY1, pRS314TEF-RtCRTI and pRS313TEF-spt15$_{(R98H)}$ was carried out (FIG. 17). It was observed with over expression of spt15$_{(R98H)}$, there was much more increase in β-carotene (3 fold) than with over expression of tHMG1 (1.7 fold), whereas the levels of phytoene with over expression of spt15$_{(R98H)}$ was less (1.6 fold) as compared with over expression of tHMG1 (2.8 fold).

The results indicate that even though the strain background had limiting GGPP conditions, it was not a requirement for the increase in flux, and even high GGPP conditions could lead to further increase isoprenoids, with the mutants isolated through this screen.

Example 8: Spt15 Mutants, Yield Increased Levels of the Sesquiterpene, α-Farnesene Level of Isoprenoid Expression Using the Expression Construct Levels of α-farnesene was quantified which is synthesized from FPP. The farnesene synthase gene from *Arabidopsis* was overexpressed in *S. cerevisiae* and levels of farnesene in presence of SPT15 mutants was estimated.

To investigate whether the isolated spt15 mutants were increasing the yield of only carotenoids through RtCRTI or if they were increasing the flux in the isoprenoid pathway in *S. cerevisiae*, we chose to examine an alternative isoprenoid, the sesquiterpene α-Farnesene (which is produced from FPP in the isoprenoid pathway) in *S. cerevisiae*. We expressed the α-Farnesene synthase gene of *A. thaliana* in *S. cerevisiae* ABC 276 strain and quantified the production of α-Farnesene.

Expression of the α-Farnesene synthase gene of *A. thaliana* produced very little amounts of α-Farnesene (0.29 μg/L/O.D) but it was adequate to test the effects of the spt15 mutants. With over expression of either tHMG1 or any of the different spt15 mutants, the yield of α-Farnesene increases upto 1.5 fold. tHMG1 also led to an approximately similar fold increase in α-Farnesene. The maximum increase in α-Farnesene was observed with over expression of spt15$_{(A101T)}$ (0.44 μg/L/O.D) (Table 5).). The increase in the levels of α-Farnesene with spt15 mutants suggests that they are increasing the flux in the isoprenoid pathway and their effects are not exclusive to the carotenoid pathway.

TABLE 5

Yield of α-Farnesene obtained in different strain backgrounds. T- TEF promoter, AtFS-α-Farnesene synthase from *Arabidopsis thaliana*

| Sr. no. | Strain Background | α-Farnesene(μg/L/O.D) |
|---|---|---|
| 1. | T$_{313}$ + T$_{AtFS}$ | 0.29 ± 0.02 |
| 2. | T$_{tHMG1}$ + T$_{AtFS}$ | 0.38 ± 0.04 |
| 3. | T$_{SPT15WT}$ + T$_{AtFS}$ | 0.24 ± 0.04 |
| 4. | T$_{SPT15(R98H)}$ + T$_{AtFS}$ | 0.37 ± 0.02 |
| 5. | T$_{SPT15(A100V)}$ + T$_{AtFS}$ | 0.39 ± 0.05 |
| 6. | T$_{SPT15(A100V)}$ + T$_{AtFS}$ | 0.44 ± 0.02 |

Example 9: V2 Assay Strain

The expression of carotenogenic genes from *R. toruloides* (red yeast) results in the production of a mixture of carotenoids owing to the bifunctional nature of some of the enzymes. As the color of each of the different carotenoids is different, the presence of these mixture of carotenoids can interfere with correlations of increased pigmentation with increased flux in the isoprenoid pathway. Hence it was attempted to develop a strain that makes a single colored carotenoid which can be then used as a more reliable marker for flux. The present study aimed at producing one carotenoid in the yeast cell so that increase in its color will better reflect the increase in the flux in the isoprenoid pathway. Lycopene being the first colored product in the carotenoid pathway, for production of lycopene in *S. cerevisiae*, three genes—pRS315TEF-RtGGPPS, pRS314TEF-AtPS and pRS314TEF-RtCRTI were transformed. It has GGPP synthase (RtGGPPS) and phytoene dehydrogenase (RtCRTI) from *R. toruloides* and phytoene synthase (AtPS) from *A. thaliana* which lacks lycopene cyclase activity. (Most other phytoene synthases including the Phytoene synthase of *R. toruloides* are bifunctional in nature and in addition to the phytoene synthase activity also contain the lycopene cyclase activity). This strain produces Lycopene (128.51±8.07 μg/g DCW) as the major carotenoid and does not produce β-carotene. When this strain was validated with over expression of known flux increaser of the isoprenoid pathway, tHMG1, an increase in the colour had been observed. The increase in the colour suggests that this strain combination can be used as assay strain for indicating the flux in the isoprenoid pathway. (or for isolation of mutants that will increase the flux in the isoprenoid pathway). This is designated as V2 assay strain. This V2 assay strain when transformed with the spt15 mutants (isolated using V1 assay strain) and transformants were dilution spotted on SD plates. An increase in the colour with spt15 mutants was observed (FIG. 18).

Advantages:

Developed a carotenoid-based visual genetic screen for increased isoprenoid flux in *Saccharomyces cerevisiae*.

*Rhodosporidium toruloides* carotenogenic genes functionally expressed in *S. cerevisiae* with high yields of β-carotene Catalytically efficient mutant of Phytoene dehydrogenase (RtCRTI A393T) isolated that yields higher β-carotene levels Isolated novel mutants of global transcription factor SPT15 that increase the yield of isoprenoids and carotenoids.

SPT15 mutants also show increase in the yield of alternative isoprenoid-α-Farnesene.

REFERENCES

Ajikumar, P. K., Xiao, W. H., Tyo, K. E., Wang, Y., Simeon, F., Leonard, E., Mucha, O., Phon, T. H., Pfeifer, B., Stephanopoulos, G., 2010. Isoprenoid pathway optimization for taxol precursor overproduction in *Escherichia coli*. Science 330, 70-74

Alper, H., Moxley, J., Nevoigt, E., Fink, G. R., Stephanopoulos, G., 2006. Engineering yeast transcription machinery for improved ethanol tolerance and production. Science (New York, N.Y.) 314, 1565-8.

Alper, H., Stephanopoulos, G., 2007. Global transcription machinery engineering: a new approach for improving cellular phenotype. Metabolic engineering 9, 258-67.

Al-Babili, S., Hoa, T. T., Schaub, P., 2006. Exploring the potential of the bacterial carotene desaturase CrtI to increase the beta-carotene content in Golden Rice. Journal of experimental botany 57, 1007-14.

Bleichenbacher, M., Tan, S., Richmond, T., 2003. Novel Interactions Between the Components of Human and Yeast TFIIA/TBP/DNA Complexes. Journal of Molecular Biology 332, 783793.

Bohlmann, J., Keeling, C. I., 2008 Terpenoid biomaterials. Plant Journal 54, 656-669.

Caniard A, Zerbe P, legrand S, Cohade A, Valot N, et al. (2012) discovery and functional characterization of two diterpene synthases for sclareol biosynthesis in *Salvia sclarea* (L.) and their relevance for perfume manufacture. BMC Plant Biol 12: 119.

Chasman, D., Flaherty, K., Sharp, P., Kornberg, R., 1993. Crystal structure of yeast TATA-binding protein and model for interaction with DNA. Proceedings of the National Academy of Sciences 90, 8174-8178.

Guo, W., Tang, H. and Zhang, L. (2014), Lycopene cyclase and phytoene synthase activities in the marine yeast *Rhodosporidium diobovatum* are encoded by a single gene crtYB. J. Basic Microbiol., 54: 1053-1061. doi: 10.1002/jobm.201300920

Hunter, W. N., 2007. The non-mevalonate pathway of isoprenoid precursor biosynthesis. Journal of Biological Chemistry 282, 21573-21577

Jiang Y; Proteau P; Poulter D; Ferro-Novick S., 1995. BTS1 encodes a geranylgeranyl diphosphate synthase in *Saccharomyces cerevisiae*. Journal of Biological Chemistry. 270, 21793-99.

Kumar, S., Kushwaha, H., Bachhawat, A., Raghava, G., Ganesan, K., 2012. Genome sequence of the oleaginous red yeast *Rhodosporidium toruloides* MTCC 457. Eukaryotic cell 11, 1083-4.

Li, Q., Sun, Z., Li, J., Zhang, Y., 2013. Enhancing beta-carotene production in *Saccharomyces cerevisiae* by metabolic engineering. FEMS microbiology letters 345, 94-101.

Misawa, N., Nakagawa, M., Kobayashi, K., Yamano, S., Izawa, Y., Nakamura, K., Harashima, K., 1990. Elucidation of the Erwiniauredovora carotenoid biosynthetic pathway by functional analysis of gene products expressed in *Escherichia coli*. Journal of bacteriology 172, 6704-12.

Moliné, M., Libkind, D., van Broock, M., 2012. Production of torularhodin, torulene, and β-carotene by *Rhodotorula* yeasts. Methods in molecular biology (Clifton, N.J.) 898, 275-83.

Nacken, V., Achstetter, T., Degryse, E., 1996. Probing the limits of expression levels by varying promoter strength and plasmid copy number in *Saccharomyces cerevisiae*. Gene 175, 253260.

Nelis, H. J., De Leenheer., A. P., 1991. Microbial sources of carotenoid pigments used in foods and feeds. J. Appl. Bacteriol. 70, 181-191

Özaydin, B., Burd, H., Lee, T. S., Keasling, J. D., 2013. Carotenoid-based phenotypic screen of the yeast deletion collection reveals new genes with roles in isoprenoid production. Metabolic engineering 15, 174-83.

Ro, D. K., Paradise, E. M., Ouellet, M., Fisher, K. J., Newman, K. L., Ndungu, J. M., Ho, K. A., Eachus, R. A., Ham, T. S., Kirby, J., Chang, M. C., Withers, S. T., Shiba, Y., Sarpong, R., Keasling, J. D., 2006. Production of the antimalarial drug precursorartemisinic acid in engineered yeast. Nature 440, 940-943.

Rose M D, Fink G R. 1987. KAR1, a gene required for function of both intranuclear and extranuclear microtubules in yeast. Cell 48: 1047-1060.

Schalk M (2011) Method for producing sclareol. US20110041218 A1. Firmenich S A

Szappanos, B., Kova´ cs, K., Szamecz, B., Honti, F., Costanzo, M., Baryshnikova, A., Gelius-Dietrich, G., Lercher, M. J., Jelasity, M., Myers, C. L., Andrews, B. J., Boone, C., Oliver, S. G., Pa´ l, C., Papp, B., 2011. An integrated approach to characterize genetic interaction networks in yeast metabolism. Nat. Genet. 43, 656-662.

Sambrook J, Fritsch E F, Maniatis T. 1989. Molecular Cloning: A Laboratory Manual. Cold Spring Harbor Press: Cold Spring, Harbor, N.Y.

Schaub, P. et al., 2012. On the structure and function of the phytoene desaturase CRTI from Pantoeaananatis, a membrane-peripheral and FAD-dependent oxidase/isomerase. PloS one 7, e39550.

Ukibe, K., Hashida, K., Yoshida, N., Takagi, H., 2009. Metabolic engineering of *Saccharomyces cerevisiae* for astaxanthin production and oxidative stress tolerance. Applied and environmental microbiology 75, 7205-11.

Verwaal R, Wang J, Meijnen J-P, Visser H, Sandmann G, van den Berg J A, et al 2007; High-level production of beta-carotene in *Saccharomyces cerevisiae* by successive transformation with carotenogenic genes from *Xanthophyllomycesdendrorhous*. Appl Environ Microbiol 73:4342-50.

Wriessnegger T and Pichler H., 2013. Yeast metabolic engineering: targeting sterol metabolism and terpenoid formation. ProgLipid Res. 52(3), 277-93.

Yamano, S., T. Ishii, M. Nakagawa, H. Ikenaga, and N. Misawa. 1994. Metabolic engineering for production of beta-carotene and lycopene in *Saccharomyces cerevisiae*. Biosci. Biotechnol. Biochem. 58:1112-1114.

Yuan, J., Ching, C. B., 2014. Combinatorial engineering of mevalonate pathway for improved amorpha-4,11-diene production in budding yeast. Biotechnology and bioengineering 111, 608-17.

Zhao, H., Li, J., Han, B., Li, X., Chen, J., 2014. Improvement of oxidative stress tolerance in *Saccharomyces cerevisiae* through global transcription machinery engineering. Journal of Industrial Microbiology & Biotechnology 41, 869-878

Zhu, Z. et al., 2012. A multi-omic map of the lipid-producing yeast *Rhodosporidiumtoruloides*. Nature communications 3, 1112.

We claim:

1. A construct comprising carotenoid genes from red yeasts transformed in Saccharomyces cerevisiae host cell for increased beta-carotenoid production as a major fraction of total carotenoids, wherein the carotenoid genes of the red yeasts are geranylgeranyl diphosphate synthase (GGPPS), phytoene synthase (PSY1) and mutant phytoene desaturase (CRT 1) where said genes are optimized for expression in the Saccharomyces cerevisiae as set forth in SEQ ID NO: 1, 2 and 3; where the Saccharomyces cerevisiae host cell comprises a mutations in the TATA binding protein spt15 and the 3-hydroxy-3-methylglutaryl-Coenzyme A reductase (HMG1) and wherein the phytoene desaturase (CRT 1) gene is mutated CRT1 (A393T) as set forth in SEQ ID NO: 3.

2. The construct as claimed in claim 1, wherein the carotenoid genes are selected from Rhodosporidium spp.

3. The construct as claimed in claim 2, wherein the rhodosporidium is preferably Rhodosporidium toruloides.

4. The construct comprising of carotenoid genes in Saccharomyces cerevisiae as claimed in claim 1, wherein the S. cerevisiae is selected from S. cerevisiae ABC276, S. cerevisiae BY4741, S. cerevisiae CEN.PK21C, S. cerevisiae CEN.PK21D, S. cerevisiae S288C, and S. cerevisiae industrial strains.

5. The construct comprising of carotenoid genes in Saccharomyces cerevisiae as claimed in claim 4, wherein the S. cerevisiae is preferably S. cerevisiae ABC276 and S. cerevisiae CEN.PK21C.

6. The construct as claimed in claim 1, wherein the carotenoid genes are cloned in yeast centromeric plasmids.

7. The construct as claimed in claim 6, wherein the promotor is selected from CYC, TEF, GPD or TDH or a combination of these.

8. The construct as claimed in claim 7, wherein the promotor may be conserved or mutated.

9. The construct as claimed in claim 1, wherein the SPT15 mutants is selected from $SPT15_{Arg98His}$, $SPT15_{Ala100Val}$, $SPT15_{Ala101Thr}$.

10. The construct as claimed in claim 1, wherein HMG1 is preferably truncated.

11. The construct as claimed in claim 1, wherein the carotenoid genes are geranylgeranyl diphosphate synthase (GGPPS), phytoene synthase (PSY1), mutated $CRTI_{A393T}$ of Rhodosporidium toruloids and BTSI of S. cerevisiae.

* * * * *

SEQUENCE LISTING

<160> NUMBER OF SEQ ID NOS: 10

<210> SEQ ID NO 1
<211> LENGTH: 1080
<212> TYPE: DNA
<213> ORGANISM: Rhodosporidium toruloides

<400> SEQUENCE: 1

| | | | | | |
|---|---|---|---|---|---|
| atgtctttgg | attggtatga | taatttcatt | gataaagttc | aaggtactcc | atcttggcaa | 60 |
| ccagctcaag | aacaagtttt | gactgaacca | tatacttatt | tggcttctat | tccaggtaaa | 120 |
| gaagttagat | ctgctttgat | tgctgctttc | aatcaatgga | tgggtgttgc | tgatgttgat | 180 |
| ttggaaattg | ttaaaagagt | tgttggtatg | ttgcatactg | cttctttgtt | gatggatgat | 240 |
| gttgaagatg | attctcattt | gagaagaggt | atgccagttg | ctcataaaat | ttatggtatt | 300 |
| ccacaaacta | ttaattctgc | taattatgtt | tatttcttgg | cttttccaaga | attgcaaaga | 360 |
| attcatccaa | gaccaggtat | taaagttgaa | gaaatggtta | ctgaagaatt | gttgaatttg | 420 |
| catagaggtc | aaggtatgga | tttgttctgg | agagaaaatt | tgatttgtcc | aactgaacca | 480 |
| gaatatattg | atatggttaa | taataaaact | ggtggtttgt | tcagaattgc | tattaaattg | 540 |
| atgatggctg | cttctccagc | tgctccaaga | gattatgttc | cattggctaa | tttgattggt | 600 |
| attattttcc | aaattagaga | tgattatgtt | aatttgcaat | ctgttgaata | tgctaataat | 660 |
| aaaggtttct | gtgaagattt | ctctgaaggt | aaattctctt | tcccaattgt | tcattctatt | 720 |
| agatctgata | cttctaatag | acaaattttg | aatattttga | gagaaagacc | atcttctcca | 780 |
| ggtccaaaag | aatatgctgt | ttcttatatg | gaaactagaa | ctggttcttt | cgcttatact | 840 |
| agagaagttt | tgagaaaaatt | gactcaacaa | gctagagatg | aagttgctag | attgggtggt | 900 |
| aatagaggtg | ttgaagctat | tttggataaa | ttggttttgg | aagaaccaca | agctagagct | 960 |
| actggtgttg | aaggtgaagc | tatggaaaga | aaattggaag | aagttgttaa | atctaaacca | 1020 |
| gttaaagctg | ttactaatgg | tgttaatggt | gttcatgctc | atgaattgcc | aaaagtttaa | 1080 |

<210> SEQ ID NO 2
<211> LENGTH: 1839
<212> TYPE: DNA
<213> ORGANISM: Rhodosporidium toruloides

<400> SEQUENCE: 2

| | | | | | |
|---|---|---|---|---|---|
| atgggtggtt | tggattattg | gttggttcat | ttgagatgga | ctattccacc | agctttggtt | 60 |
| ttgtggtcta | ctttcagaaa | attgagaact | agaagagatg | tttataaaac | tttgttcttg | 120 |
| gttgctattg | ctgttactgc | tactattcca | tgggattctt | atttgattag | acatagaatt | 180 |
| tggtcttatc | cagaatcttc | tgttgttggt | ccaacttttgt | tcgctattcc | atatgaagaa | 240 |
| atttctcttct | tcttcgttca | aacttatatt | actgctactg | tttatgcttt | gttctctaga | 300 |
| ccagttgttc | atgctgttttt | gttgccaaga | aaaccatctg | atggtagagc | tgctagatat | 360 |
| attggtactg | ctgctttctt | gggtattttc | gctttggctt | gggctaaatt | ggaagaaggt | 420 |
| ggtgaaggta | cttatttggc | tttgattgtt | ggttgggttg | ctccattctt | ggctttgttg | 480 |
| tggttcattg | cttctaatca | tttgttggct | atgccaagat | gggctgttgg | tttgccaatt | 540 |
| ttgttgccaa | ctttgtatt | gtgggaatgt | gatgctagag | ctttgcaaag | aggtacttgg | 600 |
| gttattgaaa | aaggtactaa | attgggtttg | gctttcagag | gtttggaaat | tgaagaagct | 660 |
| gttttctttct | tgttgactaa | tgttatgatt | gttttccggtt | tggttgcttg | tgattattgt | 720 |
| ttggctgttc | atgatttgag | atcttatgat | actagaactt | cttctgttttt | cccaccattg | 780 |

| | |
|---|---:|
| agagatttct tgccaattttt gttgaattct ccagatgctg ctcaaagaca aagaattgaa | 840 |
| gatttgcaag ctgctattga tattttgtct gttcattcta aatcttttctc tactgcttct | 900 |
| caagttttcg aaggtagatt gagattggat ttgttgtctt tgtatgcttg gtgtagagtt | 960 |
| tgtgatgatt tgattgataa tgcttctact gttgctgctg ctgaatctaa tattgatatg | 1020 |
| atttctggtt gtttggattt gttgtatcca ccatctgctt ctactccaac ttcttttgcca | 1080 |
| gttagagttt ctaataaaca aattgaagct gctttgccag tttgtctga accagaaaga | 1140 |
| ggtgctttcc atttgttgag attgttgcca attgctagac caccattgga tgaattgttg | 1200 |
| gatggtttca gaactgattt gtctttcttg gctttgtctg attctaaagg tgctaaaact | 1260 |
| aatggtgctg ctaatggtaa tggtaatggt aaatcttcta tttctgctga attgccaatt | 1320 |
| aaaactgatt ctgatttgtt ggtttatgct aataatgttg cttcttctgt tgctgatttg | 1380 |
| tgtgttcaat tggtttgggc tcattgtact ccatattcta gaactccagc tcaatctgtt | 1440 |
| ccaagagatc caattttgtc tgaagctgaa aatgctcatg ttttggctgc tgctagagaa | 1500 |
| atgggtcaag ctttgcaatt ggttaatatt gctagagatg ttccagctga tttgaaaatt | 1560 |
| ggtagaattt atttgccagg tagagctttg gatactccag ttccagaatt gacttctgat | 1620 |
| agaagagctt tgttggctag agctaatgaa atggctgctc attctaaaga tgctattgaa | 1680 |
| aaattgccac aagaagctag aggtggtatt agagctgctt gtttggttta tttgtctatt | 1740 |
| ggtgatgctg ttggtaaagc tttggatgaa ggtagagtta tggaaagagc tagagtttct | 1800 |
| aaaggtgcta gagctagaaa agcttggcaa gctttgtaa | 1839 |

<210> SEQ ID NO 3
<211> LENGTH: 1665
<212> TYPE: DNA
<213> ORGANISM: Rhodosporidium toruloides

<400> SEQUENCE: 3

| | |
|---|---:|
| atggctgctg ctaatggtca tggtaaaggt aaaccatctg ttttgattgt tggtgctggt | 60 |
| gttggtggta ctgcttctgc tgctagattg gctcaatctg gtttcgatgt tactgttttg | 120 |
| gaaaaaaatg atttcgctgg tggtagatgt tcttttgttca ctgatccaac taaatctttc | 180 |
| agattcgatc aaggtccatc tttgttcttg attccaagat tgttcgatga acttttcaat | 240 |
| gatttgggta cttcttttgga aaatgaaggt attaaattgg ttaaatgtga accaaaattat | 300 |
| agaattgttt tcccagataa agaagttgtt gaaatgtctt ctgatttgac tagaatgaaa | 360 |
| aaacaagttg aaagatggga aggtgaaaaa ggtttcgaag gttcttggg tttcttgaaa | 420 |
| gaaggtcatg ctcattatga aattgtctatg gttcatgttt tgcatagaaa tttcacttct | 480 |
| ttgttgtcta tggttagacc atctttgatt attcaattga gaaaattgca tccattcgtt | 540 |
| tctgtttatt ctagagctac taaatatttc aaaactgata gaatgagaag gcttttcact | 600 |
| ttcgcttcta tgtatttggg tatgtctcca ttcgatgctt ggtgctta taatttgttg | 660 |
| caatatactg aacattgtga aggtattttg tatccattgg gtggtttcgg tagaattcca | 720 |
| caaactttgc aacaattggc tgaaaaatct ggtgctaaat tcagattcaa ttctccagtt | 780 |
| aaaagagtta ctgttgaaaa tggtactgct aaaggtgttg aattggaatc tggtgaaaaa | 840 |
| ttgactgctg atattgtttt ggttaatgct gatttggttt ggtctatggc tcatttgtat | 900 |
| gaagaaactt ctattctaa agattggaa gaaagaccag tttcttgttc ttctatttct | 960 |
| ttgtattggt ctatgaatag aaaaaattcca caattggatt ctcatactat tttcttggct | 1020 |
| gaagaatata gagaatcttt cgattctatt ttcagagaac atagaattcc acatgaacca | 1080 |

```
tctttctatg ttaatgttcc atctagacat gatccatctg ctgctccagc tgataaagat    1140
gctgttattg ttttggttcc agttggtcat atttctgctg ctttgccatc ttcttctgat    1200
tgggataaag ttgttgaaga aactagaaat aaaattattg gtgaaattga agaagattg     1260 gatattgaag atttgagatc ttgtattgaa catgaaacta ttaatactcc aattacttgg    1320
ggtgaaaaat tcaatttgca tagaggttct attttgggtt tgtctcatga tttcttcaat    1380
gttttgtctt tcagaccaaa aactagacat ccatctgtta aaaatgctta tttcgttggt    1440
gcttctgctc atccaggtac tggtgttcca attgttttgg ctggtgctag attggttgct    1500
actcaaattt tgaatgattt gggtatgcca attccatcta gatggaatgt tcttcttct    1560 gaattggcta ctcataaaac tattagagat gctgctggtg gtttcacttt tgttgtctgtt   1620 ttgttcggtt tgattgcttt gttggttatg tatttgagag gttaa                    1665

<210> SEQ ID NO 4
<211> LENGTH: 723
<212> TYPE: DNA
<213> ORGANISM: Saccharomyces cerevisiae

<400> SEQUENCE: 4
atggccgatg aggaacgttt aaaggagttt aaagaggcaa acaagatagt gtttgatcca    60
aataccagac aagtatggga aaccagaat cgagatggta caaaaccagc aactactttc    120
cagagtgaag aggacataaa aagagctgcc ccagaatctg aaaagacac ctccgccaca     180 tcaggtattg ttccaacact acaaaacatt gtggcaactg tgactttggg gtgcaggtta    240
gatctgaaaa cagttgcgct acatgcccgt aatgcagaat ataaccccaa gcgttttgct    300
gctgtcatca tgcgtattag agagccaaaa actacagctt taattttgc ctcagggaaa    360 atggttgtta ccggtgcaaa aagtgaggat gactcaaagc tggccagtag aaaatatgca    420
agaattatcc aaaaaatcgg gtttgctgct aaattcacag acttcaaaat acaaaatatt    480
gtcggttcgt gtgacgttaa attccctata cgtctagaag ggttagcatt cagtcatggt    540
actttctcct cctatgagcc agaattgttt cctggtttga tctatagaat ggtgaagccg    600
aaaattgtgt tgttaatttt tgtttcagga agattgttc ttactggtgc aaagcaaagg    660
gaagaaattt accaagcttt tgaagctata taccctgtgc taagtgaatt tagaaaaatg    720
tga                                                                  723

<210> SEQ ID NO 5
<211> LENGTH: 3165
<212> TYPE: DNA
<213> ORGANISM: Saccharomyces cerevisiae

<400> SEQUENCE: 5
atgccgccgc tattcaaggg actgaaacag atggcaaagc caattgccta tgtttcaaga    60
ttttcggcga aacgaccaat tcatataata ctttttttctc taatcatatc cgcattcgct    120
tatctatccg tcattcagta ttacttcaat ggttggcaac tagattcaaa tagtgttttt    180
gaaactgctc caaataaaga ctccaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagtgttt ccaaagaaat tcttctact gatggaacga aatggaggtt aagaagtgac    480
agaaaaagtc ttttcgacgt aaagacgtta gcatattctc tctacgatgt attttcagaa    540
```

```
aatgtaaccc aagcagaccc gtttgacgtc cttattatgg ttactgccta cctaatgatg    600
ttctacacca tattcggcct cttcaatgac atgaggaaga ccgggtcaaa tttttggttg    660
agcgcctcta cagtggtcaa ttctgcatca tcactttttct tagcattgta tgtcacccaa   720
tgtattctag gcaaagaagt ttccgcatta actcttttttg aaggtttgcc tttcattgta   780
gttgttgttg gtttcaagca caaaatcaag attgcccagt atgccctgga gaaatttgaa    840
agagtcggtt tatctaaaag gattactacc gatgaaatcg ttttttgaatc cgtgagcgaa   900 gagggtggtc gtttgattca agaccatttg ctttgtattt ttgcctttat cggatgctct    960
atgtatgctc accaattgaa gactttgaca aacttctgca tattatcagc atttatccta   1020 attttttgaat tgattttaac tcctacattt tattctgcta tcttagcgct tagactggaa   1080
atgaatgtta tccacagatc tactattatc aagcaaacat tagaagaaga cggtgttgtt   1140
ccatctacag caagaatcat ttctaaagca gaaagaaat ccgtatcttc tttcttaaat    1200
ctcagtgtgg ttgtcattat catgaaactc tctgtcatac tgttgtttgt cttcatcaac   1260
ttttataact ttggtgcaaa ttgggtcaat gatgccttca attcattgta cttcgataag   1320
gaacgtgttt ctctaccaga ttttattacc tcgaatgcct ctgaaaactt taaagagcaa   1380
gctattgtta gtgtcacccc attattatat tacaaaccca ttaagtccta ccaacgcatt   1440
gaggatatgg ttcttctatt gcttcgtaat gtcagtgttg ccattcgtga taggttcgtc   1500
agtaaattag ttcttttccgc cttagtatgc agtgctgtca tcaatgtgta tttattgaat   1560
gctgctagaa ttcataccag ttatactgca gaccaattgg tgaaaactga agtcaccaag   1620
aagtctttta ctgctcctgt acaaaaggct tctacaccag tttttaaccaa taaaacagtc   1680 atttctggat cgaaagtcaa aagtttatca tctgcgcaat cgagctcatc aggaccttca   1740
tcatctagtg aggaagatga ttcccgcgat attgaaagct tggataagaa aatacgtcct   1800
ttagaagaat tagaagcatt attaagtagt ggaaatacaa acaattgaa gaacaaagag    1860 gtcgctgcct tggttattca cggtaagtta cctttgtacg ctttggagaa aaaattaggt   1920
gatactacga gagcggttgc ggtacgtagg aaggctcttt caattttggc agaagctcct   1980
gtattagcat ctgatcgttt accatataaa aattatgact acgaccgcgt atttggcgct   2040
tgttgtgaaa atgttatagg ttacatgcct ttgcccgttg tgttatagg cccccttggtt   2100 atcgatggta catcttatca tataccaatg gcaactacag agggttgttt ggtagcttct   2160
gccatgcgtg gctgtaaggc aatcaatgct ggcggtggtg caacaactgt tttaactaag   2220
gatggtatga caagaggccc agtagtccgt ttcccaactt tgaaaagatc tggtgcctgt   2280
aagatatggt tagactcaga agagggacaa aacgcaatta aaaaagcttt taactctaca   2340
tcaagatttg cacgtctgca acatattcaa acttgtctag caggagattt actcttcatg   2400
agatttagaa caactactgg tgacgcaatg ggtatgaata tgatttctaa aggtgtcgaa   2460
tactcattaa agcaaatggt agaagagtat ggctgggaag atatggaggt tgtctccgtt   2520
tctggtaact actgtaccga caaaaaacca gctgccatca actggatcga aggtcgtggt   2580
aagagtgtcg tcgcagaagc tactattcct ggtgatgttg tcagaaaagt gttaaaaagt   2640
gatgtttccg cattggttga gttgaacatt gctaagaatt tggttggatc tgcaatggct   2700
gggtctgttg gtggatttaa cgcacatgca gctaatttag tgacagctgt ttcttggca    2760 ttaggacaag atcctgcaca aaatgttgaa agttccaact gtataacatt gatgaaagaa   2820
gtggacggtg atttgagaat ttccgtatcc atgccatcca tcgaagtagg taccatcggt   2880
```

```
ggtggtactg ttctagaacc acaaggtgcc atgttggact tattaggtgt aagaggcccg    2940
catgctaccg ctcctggtac caacgcacgt caattagcaa gaatagttgc ctgtgccgtc    3000
ttggcaggtg aattatcctt atgtgctgcc ctagcagccg gccatttggt tcaaagtcat    3060
atgacccaca acaggaaacc tgctgaacca acaaaaccta acaatttgga cgccactgat    3120
ataaatcgtt tgaaagatgg gtccgtcacc tgcattaaat cctaa                   3165
```

<210> SEQ ID NO 6
<211> LENGTH: 1578
<212> TYPE: DNA
<213> ORGANISM: Saccharomyces cerevisiae

<400> SEQUENCE: 6

```
atggaccaat tggtgaaaac tgaagtcacc aagaagtctt ttactgctcc tgtacaaaag      60
gcttctacac cagttttaac caataaaaca gtcatttctg gatcgaaagt caaaagttta    120
tcatctgcgc aatcgagctc atcaggacct tcatcatcta gtgaggaaga tgattcccgc    180
gatattgaaa gcttggataa gaaaatacgt cctttagaag aattagaagc attattaagt    240
agtggaaata caaaacaatt gaagaacaaa gaggtcgctg ccttggttat tcacggtaag    300
ttacctttgt acgctttgga gaaaaaatta ggtgatacta cgagagcggt tgcggtacgt    360
aggaaggctc tttcaatttt ggcagaagct cctgtattag catctgatcg tttaccatat    420
aaaaattatg actacgaccg cgtatttggc gcttgttgtg aaaatgttat aggttacatg    480
cctttgcccg ttggtgttat aggcccctttg gttatcgatg gtacatctta tcatatacca    540
atggcaacta cagagggttg tttggtagct tctgccatgc gtggctgtaa ggcaatcaat    600
gctggcggtg gtgcaacaac tgttttaact aaggatggta tgacaagagg cccagtagtc    660
cgtttcccaa cttttgaaaag atctggtgcc tgtaagatat ggttagactc agaagaggga    720
caaaacgcaa ttaaaaaagc ttttaactct acatcaagat ttgcacgtct gcaacatatt    780
caaacttgtc tagcaggaga tttactcttc atgagattta gaacaactac tggtgacgca    840
atgggtatga atatgatttc taaaggtgtc gaatactcat taagcaaat ggtagaagag    900 tatggctggg aagatatgga ggttgtctcc gtttctggta actactgtac cgacaaaaaa    960
ccagctgcca tcaactggat cgaaggtcgt ggtaagagtg tcgtcgcaga agctactatt   1020
cctggtgatt tgtcagaaa agtgttaaaa agtgatgttt ccgcattggt tgagttgaac   1080
attgctaaga atttggttgg atctgcaatg gctgggtctg ttggtggatt taacgcacat   1140
gcagctaatt tagtgacagc tgtttttcttg gcattaggac aagatcctgc acaaaatgtt   1200
gaaagttcca actgtataac attgatgaaa gaagtggacg tgatttgag aatttccgta   1260 tccatgccat ccatcgaagt aggtaccatc ggtggtggta ctgttctaga accacaaggt   1320
gccatgttgg acttattagg tgtaagaggc ccgcatgcta ccgctcctgg taccaacgca   1380
cgtcaattag caagaatagt tgcctgtgcc gtcttggcag gtgaattatc cttatgtgct   1440
gccctagcag ccggccattt ggttcaaagt catatgaccc acaacaggaa acctgctgaa   1500 ccaacaaaaac ctaacaattt ggacgccact gatataaatc gtttgaaaga tgggtccgtc   1560
acctgcatta aatcctaa                                                1578
```

<210> SEQ ID NO 7
<211> LENGTH: 1065
<212> TYPE: DNA
<213> ORGANISM: Arabidopsis thaliana

```
<400> SEQUENCE: 7
atgtcttcaa gcttagtagc aagtccttct ggagagatag ctctttcatc tgaagagaag      60
gtttacaatg ttgtgttgaa acaagctgct ttggtgaaca acagctaag gtcttcttct     120 tatgaccttg atgtgaagaa accacaagat gttgttcttc ctgggagttt gagtttgttg    180
ggtgaagctt atgatcgatg cggtgaagtt tgcgctgaat atgctaagac gttttatctt    240
ggaactttgc ttatgacacc cgaaaggcga aggcgatttt gggcaatcta cgtttggtgt    300
agaagaactg atgaacttgt ggatgggcca aatgcttcac atataactcc catggcttta    360
gatagatggg aagcaaggtt agaagatctt ttccgtggtc gtcctttcga tatgcttgat    420
gctgctctcg ctgatacagt tgctagatac ccggtcgata ttcagccatt tcgagacatg    480
atcgaaggaa tgagaatgga cttgaagaaa tcgagatacc agaacttcga tgatctatac    540
ctttactgct actacgtcgc tggaaccgtc ggattgatga gcgttccggt tatgggaatc    600
gatcctaagt cgaaagcaac aaccgaaagt gtttacaacg ctgccttggc ccttggtata    660
gccaatcagc ttactaacat actcagagac gtaggcgaag atgcgagaag aggaagggtt    720
tatctgcctc aggatgaatt ggctcaggct ggtctttcag atgaagacat attcgccgga    780
aaagtaactg ataaatggag aaacttcatg aaaatgcagc ttaaacgagc aagaatgttc    840
ttcgacgaag ctgagaaagg cgtcaccgag ctcagtgccg ctagcagatg gcctgtatgg    900
gcttcattgc tattgtacag gagaatactg gacgagatta agcgaatga ttacaacaat     960 tttactaaga gagcttatgt ggggaaagtc aagaaaattg cagctttgcc attggcttat    1020
gctaaatcag tactaaagac ttcaagttca agactatcga tatga                    1065

<210> SEQ ID NO 8
<211> LENGTH: 1698
<212> TYPE: DNA
<213> ORGANISM: Arabidopsis thaliana

<400> SEQUENCE: 8
atgcctaaac gacaggctca acggcgtttc actcgcaaga ctgactcgaa acaccatcc      60 cagcctctgg tatcccgtcg ctctgcaaac tatcaaccgt ctctttggca gcacgaatat    120
ctcctctcgc tcggtaatac atatgtgaaa gaggacaacg tcgagagagt tacgttattg    180
aagcaggaag tgagtaaaat gctcaatgaa acggaaggtt tactcgaaca gctagagctc    240
atcgacactt tacaaaggct tggagtttct taccattttg aacaagaaat caagaagaca    300
ctaacgaatg tgcatgttaa aaatgtgcga gcacacaaaa accggataga tcgaaaccga    360
tggggagatt tatacgcgac cgcccttgag ttccgactcc taaggcaaca tggtttcagt    420
atcgcacaag atgtttttga cggaaatatt ggagttgatt tggatgataa agacatcaag    480
ggtattcttt cactatacga agcttcatat ctctcgacca gaatcgatac taaattgaaa    540
gagagcatat actatacaac aaaacgactt agaaaatttg tggaggtaaa taagaatgag    600
accaaatctt acactcttcg aaggatggtt atacatgcgt tagagatgcc gtaccaccgg    660
agagtgggaa gactagaagc aagatggtac atagaagtgt acggagagag acacgacatg    720
aaccctatct tgcttgaact cgcgaaactt gattttaatt tcgtacaagc tatccatcaa    780
gacgagctca atccctctc tagttggtgg agcaagacgg gattaacaaa acacctcgat    840
ttcgttagag atcgaataac ggagggttat ttctcgagtg ttggagtaat gtatgagccc    900
gagtttgcat atcaccgaca aatgcttaca aaggttttca tgctcattac aactatcgac    960
gatatatacg atatttatgg gacacttgag gagctccaac tattcacgac catagttgaa   1020
```

| | |
|---|---|
| aaatgggatg tgaatcgtct tgaagaactt cccaactaca tgaagttatg tttctctgc | 1080 |
| ctcgtcaacg aaatcaatca gattggatat tttgtactca gagataaagg gtttaatgtg | 1140 |
| attccttacc tcaaagaatc ttgggcagat atgtgtacaa cgttttttgaa agaggcaaag | 1200 |
| tggtataaaa gtggttacaa acctaacttc gaagaataca tgcaaaatgg ttggatctca | 1260 |
| agctcagtcc ctacaatact tctacacttg ttctgtctct tatccgacca aaccttagac | 1320 |
| attcttggct cctacaatca ctctgtagtt cgaagctccg ccaccatcct ccgtctcgct | 1380 |
| aacgatctcg ccacttcttc ggaggaatta gcgagaggcg acactatgaa atccgtacaa | 1440 |
| tgtcacatgc atgaaactgg agcttcggag gcagagtcac gcgcgtacat tcaaggaatt | 1500 |
| atcggtgtgg cttgggatga cttaaacatg gagaaaaaga gttgtaggct acatcaaggt | 1560 |
| ttcctagaag ctgcggctaa tcttggacgt gtggctcagt gcgtttatca gtacggtgat | 1620 |
| ggccatggct gtcctgacaa ggctaagacc gtcaatcatg tccggtcctt gctcgtccac | 1680 |
| cctcttccac tcaattaa | 1698 |

<210> SEQ ID NO 9
<211> LENGTH: 1588
<212> TYPE: DNA
<213> ORGANISM: Medicago truncatula

<400> SEQUENCE: 9

| | |
|---|---|
| aaacaaaatg atagtaaata tttgttttaa ggaaaaaatc ctagtagttg atatatatag | 60 |
| cttcctcctc cacattcatt tgaaagcaat accttaaaag tactactcat ctgttaaacc | 120 |
| ttcaaagtag agatagtcca atgagtatac cattttctgt ggcagcaaag ccttccatca | 180 |
| ttaggaccaa cagaaaacca tattgtagaa gatatgatgt tataacatca gaattaatca | 240 |
| tggttccaaa acataaaaca gccaccttc ctcagttgtc aaaacaagga gtttctgttg | 300 |
| ctgacctaca tgtacaagaa gttgttgaaa acagtctca gacaaacatt tttgacactc | 360 |
| tatgttctag taatttcaag ccacagtttg agcctagttt tctcaaggat gcctatgaaa | 420 |
| tgtgcagaaa tatctgttcc gagtatgcaa agacattcta tctaggaact ttgcttatga | 480 |
| ccgaagaaag acagaaggct atatgggcta tatatgtttg gtgcaggagg acagatgagc | 540 |
| ttgttgatgg tcctaatgct gactatatga gctctgctgt tcttgataga tgggaagaaa | 600 |
| gattgcatga cattttcaat ggatgtccct atgatatgct tgatgctgct cttacagata | 660 |
| caatctccaa gtttcccttg gatattaagc cttttaggga catgatagaa ggtatgagaa | 720 |
| tggatacgag gaaatcacga tacaaaaatt tcgaagaatt atatctttac tgctactatg | 780 |
| tggcgggaac tgttggtttg atgagtgttc cagtaatggg aatcgcgcca gaatccctta | 840 |
| tccctgctca aagtgtatat aaatcagcat tatatcttgg tattggaaat caactcacaa | 900 |
| acattcttag agatgtaggg gaggatgcat taagaggtag agtgtacctt ccacaagatg | 960 |
| aacttggtga gttggtttta tgtgacaatg atgttttctc aagaaaggtg agtgaaagat | 1020 |
| ggagagagtt tatgaaacag cagattgcaa gggcaagatt ctacttcaac tcggcagaag | 1080 |
| aaggagcttc tcaccttgat aaagcaagcc gttggccggt ttggtcctca ttaatattgt | 1140 |
| atcgcaaaat cttagatgca atcgaagaca acgattatga caatttgaca aaacgagctt | 1200 |
| atgtaggacg aactgagaag tttgtgtcgt tgcctgcagc ttatactaga tctctctcaa | 1260 |
| ttcccaaaac cgaatctcat gcttccttca caaggcatat gtagcaaatt tttacccaaa | 1320 |
| ggctagcgtt atttgtttat tgtgcaaaat gcataccgca aattaattaa taagaaaaaa | 1380 |
| actagctcaa tatggaccag gaaaaatact tggcttcagt tccagaaatg aaaaaccatg | 1440 |

```
gactaaacag ttttactatt catatcaaag ttagaaattc aagccatggc agcaaagatg    1500
tatgacaaaa tatatgtatg aattggtcaa gtactgtaat taaatataaa tttgatggct    1560
gtaagtgttt tgtattaaca ggcggaat                                       1588

<210> SEQ ID NO 10
<211> LENGTH: 1008
<212> TYPE: DNA
<213> ORGANISM: Saccharomyces cerevisiae

<400> SEQUENCE: 10
atggaggcca agatagatga gctgatcaat aatgatcctg tttggtccag ccaaaatgaa      60
agcttgattt caaaaccttta taatcacatc cttttgaaac ctggcaagaa ctttagacta    120
aatttaatag ttcaaattaa cagagttatg aatttgccca aagaccagct ggccatagtt    180
tcgcaaattg ttgagctctt gcataattcc agccttttaa tcgacgatat agaagataat    240
gctcccttga aaggggaca gaccacttct cacttaatct tcggtgtacc ctccactata     300
aacaccgcaa attatatgta tttcagagcc atgcaacttg tatcgcagct aaccacaaaa    360
gagcctttgt atcataattt gattacgatt ttcaacgaag aattgatcaa tctacatagg    420
ggacaaggct tggatatata ctggagagac tttctgcctg aaatcatacc tactcaggag    480
atgtatttga atatggttat gaataaaaca ggcggccttt tcagattaac gttgagactc    540
atggaagcgc tgtctccttc ctcacaccac ggccattcgt tggttccttt cataaatctt    600
ctgggtatta tttatcagat tagagatgat tacttgaatt tgaaagattt ccaaatgtcc    660
agcgaaaaag gctttgctga ggacattaca gaggggaagt tatcttttcc catcgtccac    720
gcccttaact tcactaaaac gaaaggtcaa actgagcaac acaatgaaat tctaagaatt    780
ctcctgttga ggacaagtga taaagatata aaactaaagc tgattcaaat actggaattc    840
gacaccaatt cattggccta caccaaaaat tttattaatc aattagtgaa tatgataaaa    900
aatgataatg aaaataagta tttacctgat ttggcttcgc attccgacac cgccaccaat    960
ttacatgacg aattgttata tataatagac cacttatccg aattgtga              1008
```